(12) United States Patent
Barroux

(10) Patent No.: US 7,289,943 B2
(45) Date of Patent: Oct. 30, 2007

(54) LUMPING AND DELUMPING METHOD FOR DESCRIBING HYDROCARBON-CONTAINING FLUIDS

(75) Inventor: Claire Barroux, Chaville (FR)

(73) Assignee: Institut Francais Du Petrole, 92852 Rueil Malmaison Cedex (FR)

(*) Notice: Subject to any disclaimer, the term of this patent is extended or adjusted under 35 U.S.C. 154(b) by 524 days.

(21) Appl. No.: 10/809,833

(22) Filed: Mar. 26, 2004

(65) Prior Publication Data
US 2005/0065759 A1 Mar. 24, 2005

(30) Foreign Application Priority Data
Mar. 28, 2003 (FR) .................. 03 03908

(51) Int. Cl.
| | |
|---|---|
| G06F 7/60 | (2006.01) |
| G06F 17/10 | (2006.01) |
| G06G 7/48 | (2006.01) |
| G01V 1/40 | (2006.01) |
| G01V 3/18 | (2006.01) |
| G01V 5/04 | (2006.01) |
| G01V 9/00 | (2006.01) |

(52) U.S. Cl. ................ 703/10; 703/2; 702/6; 702/13; 702/30
(58) Field of Classification Search ................ 703/2, 703/10; 702/6, 13, 30
See application file for complete search history.

(56) References Cited
U.S. PATENT DOCUMENTS
5,710,726 A 1/1998 Rowney
6,108,608 A * 8/2000 Watts, III ................ 702/30
6,128,579 A 10/2000 McCormack
6,212,488 B1 * 4/2001 Meier et al. .............. 703/12

OTHER PUBLICATIONS

Optimization of Pseudocomponent Selection for Compositional Studies of Reservoir Fluids, Joergensen et al, SPE Annual Technical Conference and Exhibition, 1995, pp. 917-927 (XP00108675).
Pseudocomponent Selection for Compositional Simulation, Newley et al, SPE 19638, 1989, pp. 117-127.
Minimum Pseudocomponent Requirements for Compositional Thermal Simulation of Heavy Oil, Lolley et al, SPE 39640, 1998 pp. 383-400.
A New Simplified Compositional Simulator, Buchwalter, et al, pp. 177188, SPE 25858, 1993.

* cited by examiner

*Primary Examiner*—Paul Rodriguez
*Assistant Examiner*—Dwin McTaggart Craig
(74) *Attorney, Agent, or Firm*—Antonelli, Terry, Stout & Kraus, LLP

(57) ABSTRACT

A lumping and delumping method is useful for estimating the properties or behavior of liquid and/or vapor hydrocarbon phases from data relative to a reference set of hydrocarbon mixtures in a series of thermodynamic states in a medium. Each one of the hydrocarbon mixtures is grouped into at least three constituents (V, I, H), considering that the gas phases resulting from separation under conditions referred to as surface conditions of each mixture do not contain (H) and that the oil phases do not contain (V). The compositions of the separation products are determined by material balance. The at least three-constituent composition of each hydrocarbon mixture is determined by combination of the products resulting from the separation in proportion to the amounts of each separation product. Delumping is performed to predict a detailed composition of a fluid in the medium.

13 Claims, 13 Drawing Sheets

LUMPING AND DELUMPING METHOD FOR DESCRIBING HYDROCARBON-CONTAINING FLUIDS

FIELD OF THE INVENTION

The present invention relates to a method referred to as lumping or pseudoisation method for describing a fluid consisting of a mixture of multiple constituents by a reduced number of constituents (at least three), and a method allowing the opposite operation, a method referred to as delumping, i.e. a method allowing to obtain the detailed composition of the fluid from the description by a reduced number of constituents.

The present invention thus refers to a modelling method:
allowing to estimate the properties or the behaviour of the liquid and/or vapour phases of mixtures of multiple components such as those encountered in situ in oil or gas reservoirs, or at the surface during production of these reservoirs, by means of a representation with a reduced number of pseudo-components,
and allowing to predict, as a function of time, the detailed composition of fluids produced during production.

The invention is particularly useful for accelerating calculations during simulation of the production of underground hydrocarbon reservoirs.

Such a model allows reservoir engineers to reduce the time required for calculation of the behaviour simulations of reservoirs under production while keeping good modelling of the exchange mechanisms between hydrocarbon phases, and to establish detailed compositional profiles, which are necessary in particular for projected dimensioning and management of surface installations, such as separators, treating plants, transport lines, etc., therefore useful for surface and process engineering.

BACKGROUND OF THE INVENTION

Modelling of flows in an oil reservoir or in an underground storage is essentially based on the application to the previously gridded reservoir (or to a portion thereof) of the well-known Darcy's law describing the flow of fluids in porous media, of material balance laws in each volume unit, of thermodynamic relations governing the evolution of the phase properties of the fluids such as viscosity, density, on initial conditions, structural closure boundary conditions and well conditions.

The model known as "Black Oil", referred to hereafter as B.O., is one of the most commonly used models in petroleum simulation. It allows to describe a compressible three-dimensional and three-phase (water-oil-gas) flow. The petroleum effluents involved in this model are generally described by a water constituent, and two constituents for the reservoir fluid, the term constituent covering here the notion of component (as H2O for water) and the notion of pseudo-component (grouping of components). The constituents involved in this model are three: a water constituent (W), a heavy hydrocarbon constituent (H) and a light hydrocarbon constituent (V). In a B.O. type model referred to as "strict", constituent (W) is present only in the water phase, constituent (H) is present only in the liquid hydrocarbon phase (referred to as oil or condensate), and constituent (V) is divided between the liquid and vapour hydrocarbon phases (gas phase). A B.O. model referred to as "extensive" differs from a "strict" B.O. model in that constituent (H) is divided between the liquid and vapour hydrocarbon phases. However, although the use of B.O. models is applicable to a large number of industrial cases, it is not advisable in a certain number of cases, in particular in the case of condensate gas reservoirs subjected to dry gas injection.

Another well-known simulation model, referred to as "compositional" model, is also used, wherein the hydrocarbon fluids are represented by a larger number of constituents, at least three, often more, the water constituent being present only in the aqueous phase. Modelling the flow of these more detailed fluids leads to calculating times that are all the longer as the number of constituents is great.

In order to allow the modelling calculations to be carried out within a reasonable period of time, the fluids in place are described as consisting of a number of components or pseudo-components that is much more reduced than the real number of components. Switching from a detailed representation of the fluids to a representation with a smaller number of constituents is carried out by means of "lumping" or "pseudoisation" operations. In the description hereafter, unless otherwise stated, the term "pseudoisation" is used for any method allowing to reduce the number of constituents.

Various pseudoisation methods have already been proposed for selecting and defining the pseudo-components, and the engineer often has to find a compromise between precision and calculating time (and cost). For simulation of the production of condensate gas reservoirs subjected to dry gas injection, representations with about 6 or 8 constituents are generally used, which leads to calculating times which are all the longer as it is often necessary to reduce the size of the grid cells to limit numerical errors and consequently to increase the number of grid cells. Considerable effort is devoted to the development of pseudoisation methods for use in the industry, which would allow to reduce even further the number of constituents while modelling the behaviour of the fluids with precision, and making it possible to obtain detailed compositional information. The operations allowing to predict the reservoir simulation results that would be obtained using finely detailed modelling (where the fluids are represented by a greater number of components) are known to the man skilled in the art as "delumping".

Patent WO-00/37,898 describes a pseudoisation method applicable to compositional simulations, based on selection of a number of "dominant" base components equal to the number of pseudo-components desired at the end of the procedure. In this method, the non-dominant components are represented in all the pseudo-components, and a particular dominant component is represented in a single pseudo-component only. The mathematical transformation on which the lumping method is based allows, by inverse transformation, to obtain the detailed compositional information. The composition of a pseudo-component taken in particular can show negative molar fractions of base constituents, as in the example given in Table E7 of the patent mentioned by way of reference. It is understandable that such a representation loses a certain physical sense when a particular pseudo-component is considered individually. This may lead to robustness problems when, as it is the case in practice with gas injection, a "local" simulation result, for example in certain grid cells, shows the disappearance of one or more of the constituents used in the dynamic simulation. Besides, implementation of the invention is described as requiring many iterative calculations and a large storage space.

Earlier publications describe pseudoisation methods also applicable to compositional simulations, wherein each pseudo-component is formed by grouping together several base constituents, a particular base constituent being represented in a single pseudo-component only. Lumping can be performed according to a selection of a priori set criteria such as those given in the aforementioned patent, or by means of an optimization procedure, for example as proposed by K. Liu in the paper "Reduce the Number of Components for Compositional Reservoir Simulation", SPE 66363, presented at the SPE Reservoir Simulation Symposium, Houston, Tex., 11-14 Feb. 2001.

A paper well-known to the man skilled in the art, written by D. E. Kenyon and G. Alda Behie, "Third SPE Comparative Solution Project: Gas Cycling of Retrograde Condensate Reservoirs", SPE 12278, Journal of Petroleum Technology, August 1987, illustrates a situation that is not exceptional: a great disparity can be observed, for the same case study, in the compositional simulation results when the simulations are carried out with different, fluid representations, and moreover with different simulation softwares. In this paper, the number of constituents ranges from 5 to 16, and the disparity of the results is in part due to the various selections of fluid compositional representations: the general tendency observed is that the smaller the number of constituents, the more the hydrocarbon liquid (referred to as oil or condensate) saturation in a particular grid cell can be underestimated, and the more the oil recovery at the surface is then overestimated.

In order to collect the detailed compositional information during a compositional reservoir simulation, delumping methods such as those described in patent WO-99/42,937 and in the paper by C. Leibovici and J. Barker "A Method for Delumping the Results of a Compositional Reservoir Simulation" SPE 49068, presented at the SPE Annual Technical Conference and Exhibition New Orleans, 27-30 Sep. 1998, can be used. The method allows to foresee the evolution of the detailed composition in time from calculations, in particular equilibrium coefficient calculations, carried out in a compositional type simulation of fluids described by a certain reduced number of pseudo-components, the number of components being at least three.

A Black Oil type representation can be considered to result from a particular pseudoisation operation providing two pseudo-components. The detailed composition of each pseudo-component, which is not useful for construction of the representation, is not known a priori, which is not a crippling obstacle in collecting detailed compositional information, by a delumping operation. Thus, patent FR-00/09, 008 describes a method allowing to foresee the evolution of the detailed composition in time from calculations carried out in a Black Oil type dynamic simulation.

The principle of the delumping stage of patents WO-99/42,937 and FR-00/09,008 is to determine, from calculations carried out during simulation, with the lumped thermodynamic representation (compositional or BO), in each grid cell and at each time interval-, coefficient $\Delta D_o$ and the n coefficients $\Delta D_p$ (i.e. n+1 coefficients, n being the number of parameters of the state equation) of a known general equation previously published in a paper by C. F. Leibovici, E. H. Stenby, K. Knudsen, "A Consistent Procedure for Pseudo-Component Delumping", Fluid Phase Equilibria, 1996, 117, 225-232:

$$\text{Ln}(K_i) = \Delta D_0 + \sum_{p=1}^{n} \Delta D_p \Pi_{pi} \tag{1}$$

where $K_i$ is the equilibrium constant of constituent i and the $\Pi_{pi}$ are fixed parameters for characterizing constituent i in the state equation for a given thermodynamic representation.

Once coefficient $\Delta D_o$ and the n coefficients $\Delta D_p$ determined, they are used to calculate the equilibrium constants of the constituents of the detailed thermodynamic representation ($N_{rb}$ components) by applying Equation (1) to the $N_{rb}$ components with their own fixed characterization parameters in the detailed thermodynamic representation.

One of the significant points of this method is that, in the delumping stage, it is not necessary to solve the $N_{rb}$ equilibrium equations associated with the state equation (equations which express the equality of the fugacities of each constituent in each phase) in the various time intervals of the dynamic flow simulation, which saves calculating time.

The paper by W. H. Goldthorpe "Simulation of Gas Injection Processes in Gas-Condensate Reservoirs Using a Binary Pseudo-Component Representation", SPE 19470, presented at the SPE Asia-Pacific Conference, Sydney, Australia, 13-15 Sep. 1989, illustrates the simulation results that can be obtained with an advanced Black Oil modelling in the case of production of a condensate gas reservoir by means of a gas injection process. The case taken as an example comes from the aforementioned publication by D. E. Kenyon and G. Alda Behie. Considering the disparity of the results in this publication, the results obtained by W. H. Goldthorpe with a Black Oil representation, by comparison with the results of a simulation performed with a detailed representation, appear to be much more coherent, but it can be seen in FIG. 8 of the paper that the solution is not satisfactory in the revaporization stage because the oil saturation in a particular grid cell (the same as in the reference paper) is very different from the saturation of the detailed compositional prediction, and seems to be truncated of negative values during eight simulated production years.

The state of the prior art is thus such that there is no simple and robust lumping method available:
allowing to reduce to three the number of pseudo-components in compositional simulations, so as to obtain notably reduced calculating times, in particular for simulation of gas injection cases with revaporization effects, difficult to treat with a Black Oil representation,
guaranteeing a physical sense to the compositional simulation results and, consequently, to the associated delumping operation results.

SUMMARY OF THE INVENTION

The pseudoisation method according to the invention allows to estimate the properties or the behaviour of liquid and/or vapour hydrocarbon phases from data relative to a reference set consisting of hydrocarbon mixtures in a series of thermodynamic states resulting from the production conditions encountered, or expected as such, for underground hydrocarbon reservoirs. It comprises the following stages:
grouping each one of said hydrocarbon mixtures into at least three constituents (V, I, H), none of these constituents corresponding to a particular selection of base components or pseudo-components that would be used for a detailed compositional description of the fluids, considering that the gas phases resulting from the separation under surface conditions of each one of the hydrocarbon mixtures are mixtures from which third constituent (H) is excluded, and that the oil phases resulting from the separation under surface conditions of each one of the hydrocarbon mixtures are mixtures from which first constituent (V) is excluded, determining by material balance the compositions of the separation products comprising, for the gaseous products, at least the first and the second constituent (V, I) in variable proportions and, for the liquid products, at least the second and the third constituent (I, H) in variable proportions, and determining the at least three-constituent composition of each hydrocarbon mixture of the reference set by combination of the products of the separation thereof in proportion to the amounts of each separation product.

According to an implementation mode, each one of the hydrocarbon mixtures is grouped into only three constituents (V, I, H), the gas phases resulting from said separation are mixtures in variable proportions of first constituent (V) and of second constituent (I), the oil phases resulting from said separation are mixtures in variable proportions of second constituent (I) and of third constituent (H), and the three-constituent composition is determined.

The surface conditions are those encountered or expected during production of the reservoir, but they can be redefined depending on the context of the study carried out, and they can therefore be different from the surface conditions encountered or expected during production of the reservoir.

According to an implementation detail, the material balance is a mass balance and a molar mass is assigned to each one of the three constituents (V, I, H) after quantitative analysis of the molar masses of the separation products of the reference set.

According to an implementation variant, the data necessary for equilibrium calculation and for modelling the phase properties in the lumped representation are defined using the compositions of the phases in the lumped representation and known or estimated a priori data relative to at least the density and the viscosity of the oil and gas phases at equilibrium belonging to the reference set.

When said data includes detailed compositional data of the phases previously represented by a "detailed" state equation, the parameters of a first (and possibly single) state equation of the lumped representation, used for modelling the phase properties, are defined using this compositional data.

According to another preferred implementation variant, the parameters of a second state equation of the lumped representation, useful for equilibrium calculations, are adjusted in order to reproduce the equilibrium coefficients of the lumped representation.

To perform this adjustment, the parameters are used for example per constituent of the lumped representation in a state equation useful for calculation of the phase properties.

According to another implementation variant useful in particular for later delumping calculations, the equilibrium coefficients of the fluids are determined in a detailed compositional representation, from variables and/or parameters involved in the calculation of the phase properties, from the moment that the parameters useful for calculation of the phase properties in the lumped representation have been estimated so as to reproduce the parameters of the phases in the state equation of the detailed compositional description.

The method can also comprise delumping stages for predicting as a function of time, and in at least one thermodynamic zone, a detailed composition of a fluid contained in a hydrocarbon reservoir or produced by at least one well, these stages being for example as follows:

representing the reservoir in form of a network of grid cells (m) wherein each one forms an elementary volume filled with fluids in form of one or more phases, with at least one non-aqueous phase, defining, for each thermodynamic zone or range, the fluids by a detailed base representation, so as to determine the amount of each base constituent (i) in each hydrocarbon phase in each grid cell (m) at the time defined as initial for the delumping calculation, per thermodynamic zone for which a lumped representation of the fluids is selected, determining a state equation constructed prior to dynamic reservoir simulation with the lumped representation, to reproduce the phase parameters, in the state equation of the detailed representation, of the hydrocarbon fluids along thermodynamic paths considered to be representative of those that will be followed by the hydrocarbon fluids during the gridded simulation, carrying out, at a time interval t, a compositional simulation with a limited number of constituents wherein the phase properties are calculated by a state equation, said simulation allowing to calculate at least in each grid cell (m) and at consecutive time intervals a pressure for a hydrocarbon phase, the temperature when it varies, the flow rates of the phases between grid cells, between perforated grid cells and well, and the values of parameters and/or phase properties involved in the formal expression of the equilibrium coefficients of the detailed representation, and storing these various quantities, estimating at the next time interval (t+1) the molar fraction of each constituent i in the global detailed composition of the hydrocarbon fluid in grid cell (m) by material balance on grid cell (m), determining, using the quantities stored, at the same time interval (t+1) and in each grid cell (m), the equilibrium coefficients of each constituent (i) in the detailed representation, determining, in the same time interval (t+1), the vaporized fraction in each grid cell (m), and estimating the detailed composition of each hydrocarbon phase, at the same time interval (t+1) and in each grid cell (m), in particular in form of the numbers of moles of each constituent i in the detailed representation in each phase at the same time interval (t+1).

In other words, the essential points of the pseudoisation method can also be defined as follows:

Having data, at least density and viscosity data, available concerning oil and gas phases at equilibrium in situ for a certain number of thermodynamic states 'e' under pressure and temperature conditions $P^e$ and $T^e$, knowing directly or by means of previous calculations the molar masses of the oil phases resulting from the separation of the oil in situ, from the separation of the gas in situ, respectively denoted by $(MM_{O_O}^e)$ and $(MM_{G_O}^e)$, the molar masses of the gas phases at the surface resulting from the separation of the oil in situ, from the separation of the gas in situ, respectively denoted by $(MM_{O_G}^e)$ and $(MM_{G_G}^e)$, and the vapour molar fractions (or gas phase molar fraction), $\theta_{O_O}^e$ for the separation of the oil in situ, $\theta_{G_O}^e$ for the separation of the gas in situ, determining the compositions of the phases "at the surface", and consequently the equilibrium coefficients, in the lumped representation using constituents (V, I, H) with the assumption that the gas phases at the surface can contain constituents (V) and (I), to the exclusion of constituent (H), and that the oil phases at the surface can contain constituents (I) and (H), to the exclusion of constituent (V), determining the compositions of the phases "in situ" in the lumped representation using constituents (V, I, H) by recombination of the compositions of the phases at the surface using the vapour molar fractions $\theta_{O_O}^e$, $\theta_{G_O}^e$, these determinations providing the equilibrium coefficients of constituents (V, I, H) under the "in situ" reservoir conditions, using the a priori known data and the compositions of the phases in the lumped representation to define the input necessary for modelling the phase properties and for the equilibrium calculations in the lumped representation and, more particularly when the a priori data includes detailed compositional data of the phases previously represented by a state equation, using this additional information to define the parameters of a state equation of the lumped representation useful first for modelling the phase properties, and possibly for defining the parameters of a second state equation of the lumped representation useful for equilibrium calculations.

Constituents V, I, H are respectively related to a volatile constituent, an intermediate constituent and a heavy constituent, without any of them corresponding to a particular selection of base components or pseudo-components that would serve for a detailed compositional description of the fluids.

The essential idea implemented for delumping compositional simulations is to calculate the equilibrium coefficients of the fluids in the detailed compositional representation from variables and/or parameters involved in the phase properties calculation from the moment that the parameters useful for calculation of the phase properties in the lumped representation have been estimated so as to reproduce the parameters of the phases in the state equation of the detailed compositional description.

BRIEF DESCRIPTION OF THE FIGURES

Other features and advantages of the method according to the invention will be clear from reading the description hereafter of a non limitative embodiment example, with reference to the accompanying drawings wherein.

DETAILED DESCRIPTION

Preamble

Figure 1:
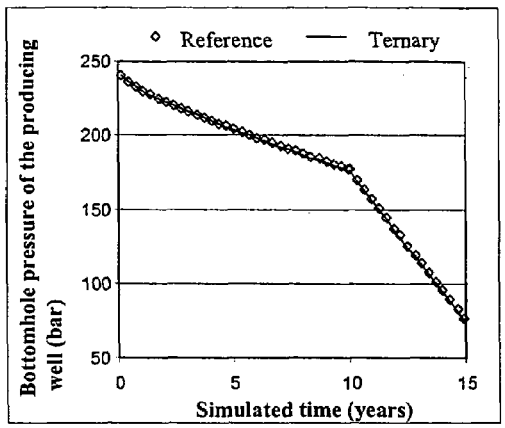
FIGS. 1-4 compare the results of a compositional simulation with a three pseudo-component representation (results referred to as ternary), obtained by applying the method according to the invention, with the results of a detailed compositional simulation with sixteen base constituents (results referred to as reference)

Modelling the behaviour of fluid mixtures requires a definition mode for the constituents used to describe the composition of the fluids and comprises:

thermodynamic equilibrium calculations to know if, under given pressure and temperature conditions, the state of equilibrium of a mixture, characterized by a global composition, is a single-phase state, or if the mixture divides into different phases, the equilibrium calculation then allowing to know the proportions of each phase, and the composition of each phase. An equilibrium calculation on a mixture, whose global composition is described by the molar fractions $z_i$ of each constituent (i), leads to determination of the vapour fraction $\theta$ and determination of the composition of each phase. The vapour fraction $\theta$ is generally determined by solving the Rachford-Rice equation known to specialists, which is applied for example in the following document:

Rachford, H. H. Jr and Rice, J. D.: "Procedure for Use of Electronic Digital Computers in Calculating Flash Vaporization Hydrocarbon Equilibrium", J. Pet. Technol., 1952, 14, 19, $$\sum_i \frac{z_i(K_i - 1)}{1 + (K_i - 1)\theta} = 0 \qquad (2)$$

the compositions of the "oil" and "gas" phases, respectively described by the molar fractions $x_i$ and $y_i$, being determined by:

$$x_i = \frac{z_i}{1 + (K_i - 1)\theta}; \; y_i = \frac{K_i z_i}{1 + (K_i - 1)\theta}. \qquad (3)$$

A hydrocarbon phase is referred to as undersaturated at a given pressure and temperature T when it is not at equilibrium with another hydrocarbon phase. According to a convention often admitted by the man skilled in the art, an undersaturated hydrocarbon phase is referred to as "oil" (or "condensate") when its critical temperature is below temperature T, and it is referred to as "gas" when its critical temperature is above temperature T. When its critical temperature is equal to temperature T, the phase can be referred to, in principle indiscriminately, as "oil" or "gas", and it is therefore considered to be related to one or to the other "oil" or "gas" qualities.

phase properties calculations such as density, viscosity, if need be, delumping calculations allowing to reproduce detailed compositional information when the fluids have been modelled in a non detailed way.

The various stages of the modelling method proposed are presented hereafter, the presentation being structured in five subchapters:
constituents definition mode,
phase properties,
thermodynamic equilibria,
delumping,
comments concerning the generalization of the approach.

Constituents Definition Mode a) We consider a set "E", referred to as reference set, of non aqueous fluids, referred to as hydrocarbon mixtures' even though they may contain certain components other than hydrocarbons, such as nitrogen, carbon dioxide, sulfur dioxide, likely to correspond to:

the undersaturated hydrocarbon fluid phases found, assumed or predicted in one or more thermodynamic zones of the reservoir considered, the hydrocarbon fluid phases at equilibrium found, assumed or predicted in one or more thermodynamic zones of the reservoir considered, the hydrocarbon fluid phases corresponding to the hydrocarbon fluids injected (or assumed to be) in the reservoir. In the most frequent practical cases, the injection fluids are gases which mainly contain light and intermediate hydrocarbons.

b) When the necessary data is available, a detailed representation with $N_{rb}$ base components and/or pseudo-components is defined to characterize the fluid mixtures. This situation being very common, the rest of the presentation is placed in such a situation because it allows to progressively introduce the usual conventions useful for the description of the method.

Number $N_{rb}$ being typically above 10, each constituent is described by a certain number of parameters, including its molar mass $MM_i$, subscript i being the number assigned to the constituent (i=, ..., $N_{rb}$). The molar fractions $x_i$ and $y_i$ respectively describe the composition of the liquid ("oil") and vapour ("gas") hydrocarbon phases in the base representation.

An element 'e' of set "E" is then described by: a pressure $P^e$, a temperature $T^e$, and:
$(2 \times N_{rb})$ molar fractions $$(x_1^e \ldots x_{Nrb}^e) \text{ and } (y_1^e \ldots y_{Nrb}^e)$$

when two hydrocarbon phases at equilibrium coexist, or $(N_{rb})$ molar fractions $$(x_1^e \ldots x_{Nrb}^e) \text{ or } (y_1^e \ldots y_{Nrb}^e)$$

when a single undersaturated hydrocarbon (oil or gas) phase is present.

The equations given hereafter are written for an element 'e' where two liquid and vapour phases coexist. For an element 'e' where a single undersaturated phase is present, the set of equations relative to the single phase represented simply has to be selected.

c) We consider that we have, for each phase of the reference set "E", fluid data likely to correspond to the compositions of the found, assumed or predicted hydrocarbon fluid phases corresponding to the fluid mixtures produced by a separation chain, and the separation chain can be reduced to a single expansion or comprise one or more intermediate separation stages. A separation chain is here, as it is usual in reservoir engineering, considered to be defined by the pressure and temperature values of the separation stages. It is convenient to consider the existing or planned separation chain through which the fluid mixture is or is assumed to be produced. In some practical cases, different separation chains can be considered, for example a different separation chain per thermodynamic zone, or a separation chain change in a given thermodynamic zone. We simplify hereafter first the presentation by considering a single separation chain identical for all the elements of set "E", then we consider the case of several separation chains.

The separation products of an oil phase of composition $$(x_1^e \ldots x_{Nrb}^e)$$

are generally a liquid phase (oil phase) and a vapour phase (gas phase) whose molar masses are assumed to be known and respectively denoted by $MM_{O_O}^e$ and $MM_{O_G}^e$, in the molar proportions assumed to be known of $\theta_O^e$ of vapour phase and $(1-\theta_O^e)$ of liquid phase. $\theta_O^e$ can take all the real values between 0.0 and 1.0, boundaries included. Subscript o (in bold type) reminds that these are separation products of the oil phase. Subscripts O and, G (not in bold type) give the oil or gas quality of the separation product.

The separation products of a gas phase of composition $$(y_1^e \ldots y_{Nrb}^e)$$

are generally a liquid phase (oil phase) and a vapour phase (gas phase) whose molar masses are assumed to be known and respectively denoted by $MM_{GO}^e$ and $MM_{GO}^e$, in the molar proportions assumed to be known of $\theta_G^e$ of vapour phase and $(1-\theta_G^e)$ of liquid phase. $\theta_G^e$ can take all the real values between 0.0 and 1.0, boundaries included. Subscript G (in bold type) reminds that these are separation products of the gas phase.

In connection with the distinct separation of an oil phase and of a gas phase at equilibrium in the reservoir, in the general situation, the (simple or complex) separation of an initially single-phase mixture, liquid (oil) or gas, produces two phases, one gaseous, the other liquid.

The following relations express the mass conservation during separation operations of respectively the oil and/or the gas from element 'e':

$$\begin{cases} MM_O^e = (1-\theta_O^e) MM_{OO}^e + \theta_O^e MM_{OG}^e \\ MM_G^e = (1-\theta_G^e) MM_{GO}^e + \theta_G^e MM_{GG}^e \end{cases} \quad (4)$$

where $MM_O^e$ and $MM_G^e$ are the molar masses of the oil and gas phases of an element 'e'.

d) The pseudoisation method provided consists in describing each hydrocarbon phase of set "E" in at least three constituents (V, I, H).

The pseudo-components are defined by considering a hypothesis denoted hereafter by "M", according to which the gas phases resulting from the separation under surface conditions of each one of the hydrocarbon mixtures are mixtures from which third constituent (H) is excluded, and that the oil phases resulting from the separation under surface conditions of each one of the hydrocarbon mixtures are mixtures from which first constituent (V) is excluded.

Constituents (V), (I), (H) are respectively related to a volatile, intermediate and heavy constituent, without any one of them corresponding to a particular selection of base components or pseudo-components that would serve for a detailed compositional description of the fluids. The associated modelling is referred to hereafter as BRO, which is short for BROWN OIL, which evokes the colour of the oil that changes from black to brown with an increasing proportion of intermediate constituents.

First of all, to facilitate the presentation, we consider, according to a restrictive interpretation of the master hypothesis "M", that the mixtures produced by the separation chain are:

a mixture in variable proportions of the volatile (V) and intermediate (I) pseudo-constituents for a gaseous product (the molar mass of constituent V being less than the molar mass of constituent I), and a mixture in variable proportions of the intermediate (I) and heavy (H) pseudo-constituents for a liquid product (the molar mass of constituent I being less than the molar mass of constituent H).

The restriction on hypothesis "M" will be lifted in paragraph tt).

The following relations therefore apply:

$$\begin{cases} MM_{OO}^e = x_{OI}^e MM_I + x_{OH}^e MM_H; & x_{OI}^e + x_{OH}^e = 1 \\ MM_{OG}^e = y_{OV}^e MM_V + y_{OI}^e MM_I; & y_{OV}^e + y_{OI}^e = 1 \\ MM_{GO}^e = x_{GI}^e MM_I + x_{GH}^e MM_H; & x_{GI}^e + x_{GH}^e = 1 \\ MM_{GG}^e = y_{GV}^e MM_V + y_{GI}^e MM_I; & y_{GV}^e + y_{GI}^e = 1 \end{cases} \quad (5)$$

For the ternary representation to retain a physical sense, it is necessary that
molar masses $MM_V$, $MM_I$, $MM_H$ are defined positive,
molar fractions $x_{OI}^e$, $x_{OH}^e$, $y_{OV}^e$, $y_{OI}^e$, $x_{GI}^e$, $x_{GH}^e$, $y_{GV}^e$, $y_{GI}^e$
range between 0.0 and 1.0, boundaries included.

It results therefrom that the selection of molar masses $MM_V$, $MM_I$, $MM_H$ has to meet the following inequalities:

$$MM_V \leq \text{Min}\{MM_{GG}^e, MM_{OG}^e\}|_{(e \in E)}$$

$$\text{Max}\{MM_{GG}^e, MM_{OG}^e\}|_{(e \in E)} \leq MM_I \leq \text{Min}\{MM_{GO}^e, MM_{OO}^e\}|_{(e \in E)}$$

$$MM_H \geq \text{Max}\{MM_{GO}^e, MM_{OO}^e\}|_{(e \in E)}$$

In the previous equations, the braces denote a set of values on which a minimum (Min) or maximum (Max) value is sought.

The inequalities being non strict, the absence of one of constituents (V, I) in a given gaseous separation product is possible, but it is not a general rule and, similarly, the absence of one of constituents (I, H) in a given liquid separation product is possible but it is not a general rule.

e) The values of the molar masses of constituents (V), (I), (H) have to be selected while meeting the above conditions and they must all be different from one another. In the example given by way of illustration, we have set down, by analogy with a Black Oil approach, without it being a limitative embodiment example:

$$MM_V \equiv \text{Min}\{MM_{GG}^e, MM_{OG}^e\}|_{(e \in E)}; \quad MM_H \equiv \text{Max}\{MM_{GO}^e, MM_{OO}^e\}|_{(e \in E)}.$$

The illustration example, widely used in the rest of the description hereafter under the designation of 'SPE3' case, corresponds to the first test case of the aforementioned publication by D. E. Kenyon and G. Alda Behie relating to the production of a condensate gas reservoir by gas cycling.

f) Once the molar masses of constituents (V), (I) and (H) defined, the composition of the fluids from the separation chain considered at c) is deduced, by the hypotheses of paragraph d) and Equations (5), by:

$$\begin{cases} x_{OV}^e = 0; & x_{OI}^e = \dfrac{MM_H - MM_{OO}^e}{MM_H - MM_I}; & x_{OH}^e = \dfrac{MM_{OO}^e - MM_I}{MM_H - MM_I} \\ y_{OV}^e = \dfrac{MM_I - MM_{OG}^e}{MM_I - MM_V}; & y_{OI}^e = \dfrac{MM_{OG}^e - MM_V}{MM_I - MM_V}; & y_{OH}^e = 0 \\ x_{GV}^e = 0; & x_{GI}^e = \dfrac{MM_H - MM_{GO}^e}{MM_H - MM_I}; & x_{GH}^e = \dfrac{MM_{GO}^e - MM_I}{MM_H - MM_I} \\ y_{GV}^e = \dfrac{MM_I - MM_{GG}^e}{MM_I - MM_V}; & y_{GI}^e = \dfrac{MM_{GG}^e - MM_V}{MM_I - MM_V}; & y_{GH}^e = 0 \end{cases} \quad (6)$$

g) The composition of the phases of element 'e' in the three-constituent representation is obtained using the following relations (where a notation in bold type is used to denote the molar fractions of the fluids in situ), which translate the molar conservation during separation operations respectively of the oil and/or the gas of from element 'e':

$$\begin{cases} x_K^e = (1 - \theta_O^e) x_{OK}^e + \theta_O^e y_{OK}^e \\ y_K^e = (1 - \theta_G^e) x_{GK}^e + \theta_G^e y_{GK}^e \end{cases} \quad K = V, I, H \quad (7)$$

By introducing relations (6) in the set of equations (7), we obtain in the reservoir for an oil phase of element 'e' the following composition:

$$\begin{cases} x_V^e = \theta_O^e \dfrac{MM_I - MM_{OG}^e}{MM_I - MM_V} \\ x_I^e = (1 - \theta_O^e)\dfrac{MM_H - MM_{OO}^e}{MM_H - MM_I} + \theta_O^e \dfrac{MM_{OG}^e - MM_V}{MM_I - MM_V} \\ x_H^e = (1 - \theta_O^e)\dfrac{MM_{OO}^e - MM_I}{MM_H - MM_I} \end{cases} \quad (8)$$

and for a gas phase:

$$\begin{cases} y_V^e = \theta_G^e \dfrac{MM_I - MM_{GG}^e}{MM_I - MM_V} \\ y_I^e = (1 - \theta_G^e)\dfrac{MM_H - MM_{GO}^e}{MM_H - MM_I} + \theta_G^e \dfrac{MM_{GG}^e - MM_V}{MM_I - MM_V} \\ y_H^e = (1 - \theta_G^e)\dfrac{MM_{GO}^e - MM_I}{MM_H - MM_I} \end{cases} \quad (9)$$

h) After stages a) to g), we thus have, for later use, minimum data for defining constituents (V), (I), (H), i.e. their molar masses.

It can be noted that, for all of the elements 'e' corresponding to states of equilibrium between hydrocarbon phases, we have, from the sets of equations (8) and (9), the equilibrium coefficients of each constituent (V), (I), (H)

$$\begin{cases} K_V^e = \dfrac{y_V^e}{x_V^e} = \dfrac{\theta_G^e}{\theta_O^e} \dfrac{MM_I - MM_{GG}^e}{MM_I - MM_{OG}^e} \\ K_I^e = \dfrac{y_I^e}{x_I^e} = \dfrac{(1 - \theta_G^e)\dfrac{MM_H - MM_{GO}^e}{MM_H - MM_I} + \theta_G^e \dfrac{MM_{GG}^e - MM_V}{MM_I - MM_V}}{(1 - \theta_O^e)\dfrac{MM_H - MM_{OO}^e}{MM_H - MM_I} + \theta_O^e \dfrac{MM_{OG}^e - MM_V}{MM_I - MM_V}} \\ K_H^e = \dfrac{y_H^e}{x_H^e} = \dfrac{1 - \theta_G^e}{1 - \theta_O^e} \dfrac{MM_{GO}^e - MM_I}{MM_{OO}^e - MM_I} \end{cases} \quad (10)$$

It can also be noted that the set of equations (6) defines the equilibrium coefficients for the outlet conditions, in pressure and temperature, of the separation chain considered in paragraph c):

$$\begin{cases} K_{OV}^e = \dfrac{y_{OV}^e}{x_{OV}^e} = \infty; \quad K_{OI}^e = \dfrac{y_{OI}^e}{x_{OI}^e} = \dfrac{MM_{OG}^e - MM_V}{MM_H - MM_{OO}^e}\dfrac{MM_H - MM_I}{MM_I - MM_V}; \quad K_{OH}^e = \dfrac{y_{OH}^e}{x_{OH}^e} = 0 \\ K_{GV}^e = \dfrac{y_{GV}^e}{x_{GV}^e} = \infty; \quad K_{GI}^e = \dfrac{y_{GI}^e}{x_{GI}^e} = \dfrac{MM_{GG}^e - MM_V}{MM_H - MM_{GO}^e}\dfrac{MM_H - MM_I}{MM_I - MM_V}; \quad K_{GH}^e = \dfrac{y_{GH}^e}{x_{GH}^e} = 0 \end{cases} \quad (11)$$

i) Set of equations (7), written for constituents (V) and (H) respectively, gives the following relations:

$$\begin{cases} x_V^e = \theta_O^e y_{OV}^e; \quad x_H^e = (1 - \theta_O^e) x_{OH}^e \\ y_V^e = \theta_G^e y_{GV}^e; \quad y_H^e = (1 - \theta_G^e) x_{GH}^e \end{cases} \quad (12)$$

from which it follows:

$$\begin{cases} y_{OV}^e = \dfrac{x_V^e}{\theta_O^e}; \quad x_{OH}^e = \dfrac{x_H^e}{1 - \theta_O^e} \\ y_{GV}^e = \dfrac{y_V^e}{\theta_G^e}; \quad x_{GH}^e = \dfrac{y_H^e}{1 - \theta_G^e} \end{cases} \quad (13)$$

then:

$$\begin{cases} y_{OI}^e = 1 - \dfrac{x_V^e}{\theta_O^e}; \quad x_{OI}^e = 1 - \dfrac{x_H^e}{1 - \theta_O^e}; \quad K_{OI}^e = \dfrac{1 - \dfrac{x_V^e}{\theta_O^e}}{1 - \dfrac{x_H^e}{1 - \theta_O^e}} \\ y_{GI}^e = 1 - \dfrac{y_V^e}{\theta_G^e}; \quad x_{GI}^e = 1 - \dfrac{y_H^e}{1 - \theta_G^e}; \quad K_{GI}^e = \dfrac{1 - \dfrac{y_V^e}{\theta_G^e}}{1 - \dfrac{y_H^e}{1 - \theta_G^e}} \end{cases} \quad (14)$$

Set of equations (14) shows that, from the moment that the molar masses of constituents (V), (I), (H) are fixed, and that the compositions of the phases of an element 'e' in the ternary representation have been established, the equilibrium coefficients of constituent (I) can be obtained from the sole knowledge of the molar fractions of constituents (V) and (H) in the oil and gas phases of element 'e' and of the vapour fractions $\theta_O^e$ and $\theta_G^e$ at the outlet of the separation chain for each phase. A first implication is that, in case of multiple separation chains, it is possible to generate the equilibrium coefficient data of constituent (I) relative to a separation chain (referred to as CS_B hereafter) other than the chain used to obtain the oil and gas compositions of element 'e' (referred to as CS_A hereafter). This is diagrammatically shown in the following table:

| Detailed mixture | Operation | Data used | Ternary mixture | Equilibrium coefficients CS_B |
|---|---|---|---|---|
| $(x_1^e \ldots x_{Nrb}^e)\zeta$ | $\xrightarrow{CS\_A}$ | $\{MM_{OO}^e, MM_{OG}^e, \theta_O^e\}_{CS\_A}$ | $\{x_V^e, x_I^e, x_H^e\}_{CS\_A}$ | $K_{OI}^e = \dfrac{1 - \dfrac{x_{V\,CS\_A}^e}{\theta_{O\,CS\_B}^e}}{1 - \dfrac{x_{H\,CS\_A}^e}{1 - \theta_{O\,CS\_B}^e}}$ |
|  | $\xrightarrow{CS\_B}$ | $\{\theta_O^e\}_{CS\_B}$ | $\rightarrow$ |  |
| $(y_1^e \ldots y_{Nrb}^e)\zeta$ | $\xrightarrow{CS\_A}$ | $\{MM_{GO}^e, MM_{GG}^e, \theta_G^e\}_{CS\_A}$ | $\{y_V^e, y_I^e, y_H^e\}_{CS\_A}$ | $K_{GI}^e = \dfrac{1 - \dfrac{y_{V\,CS\_A}^e}{\theta_{G\,CS\_B}^e}}{1 - \dfrac{y_{H\,CS\_A}^e}{1 - \theta_{G\,CS\_B}^e}}$ |
|  | $\xrightarrow{CS\_B}$ | $\{\theta_G^e\}_{CS\_B}$ | $\rightarrow$ |  |

The conditions required for such a procedure are the observance of the following inequalities $y^e_{OI\,CS\_B} \geq 0$ et $x^e_{OI\,CS\_B} \geq 0$ hence $x^e_{V\,CS\_A} \leq \theta^e_{O\,CS\_B} \leq 1 - x^e_{H\,CS\_A}$ $y^e_{GI\,CS\_B} \geq 0$ et $x^e_{GI\,CS\_B} \geq 0$ hence $y^e_{V\,CS\_A} \leq \theta^e_{G\,CS\_B} \leq 1 - y^e_{H\,CS\_A}$ It can be noted that the equilibrium coefficients of constituent (I) thus established are not formally equivalent to the coefficients that would be obtained by applying sets of equations (6) to (11) to separation chain CS_B, knowing molar masses $\{MM_{GG}^e, MM_{OO}^e, MM_{OG}^e\}_{CS\_B}$, and these molar masses must satisfy, in relation to the molar masses of constituents (V), (I), (H), the inequalities described in paragraph d).

If need be, it is possible to review the selection of the molar masses of constituents (V), (I), (H) by taking into account the molar masses of the phases resulting from separation CS_B in the writing of the inequalities of paragraph d).

j) By way of example, the non limitative procedure followed to obtain the BRO representation for the 'SPE3' case presented as an illustration consisted in various stages:

generating with a thermodynamic simulator such as, for example, the simulator known as 'PVT PACKAGE', a set of states '$e_d$' by means of a depressurization operation at constant volume at the reservoir temperature (93.3° C.), from the fluid saturation pressure (237.4 bars) down to 69 bars, using a Peng-Robinson state equation, very commonly used within the petroleum context, for the detailed 16-constituent fluid whose initial composition and parameters are given in Table 1 hereafter:

TABLE 1

SPE3 case - Reference description of the reservoir fluid

| Name | Molar fraction | MM | $T_c$ ° F. | $P_c$ psi | $V_c$ ft³/lbm | $\omega$ | $\delta_{KK'}$(*) | N2 | C1 | CO2 | C2 | C3 |
|---|---|---|---|---|---|---|---|---|---|---|---|---|
| N2 | .0194 | 28.016 | −232.33 | 492.84 | 1.4433 | 0.0350 | N2 | 0.000 | # | # | # | # |
| C1 | .6599 | 16.043 | −115.76 | 672.98 | 1.5858 | 0.0130 | C1 | 0.120 | 0.000 | # | # | # |
| CO2 | .0121 | 44.010 | 88.07 | 1069.7 | 1.5057 | 0.2250 | CO2 | 0.000 | 0.15000 | 0.000 | # | # |
| C2 | .0869 | 30.070 | 90.34 | 709.67 | 2.3707 | 0.1050 | C2 | 0.120 | 0.00000 | 0.150 | 0.000 | # |
| C3 | .0591 | 44.097 | 206.28 | 617.28 | 3.2037 | 0.1520 | C3 | 0.120 | 0.00000 | 0.150 | 0.000 | 0.000 |
| IC4 | .0239 | 58.124 | 274.96 | 528.95 | 4.2129 | 0.1918 | IC4 | 0.120 | 0.00000 | 0.150 | 0.000 | 0.000 |
| C4 | .0278 | 58.124 | 305.64 | 550.56 | 4.1007 | 0.2010 | C4 | 0.120 | 0.00000 | 0.150 | 0.000 | 0.000 |
| IC5 | .0157 | 72.151 | 370.11 | 483.41 | 4.9337 | 0.2060 | IC5 | 0.120 | 0.00000 | 0.150 | 0.000 | 0.000 |
| C5 | .0112 | 72.151 | 385.92 | 489.36 | 4.9817 | 0.2520 | C5 | 0.120 | 0.00000 | 0.150 | 0.000 | 0.000 |
| C6 | .0181 | 84.000 | 452.25 | 468.47 | 5.9268 | 0.2809 | C6 | 0.120 | 0.03000 | 0.150 | 0.010 | 0.010 |
| C7 | .0144 | 100.205 | 512.64 | 396.68 | 6.9200 | 0.3520 | C7 | 0.120 | 0.03000 | 0.150 | 0.010 | 0.010 |
| C8 | .0150 | 114.232 | 564.64 | 362.02 | 7.8811 | 0.3992 | C8 | 0.120 | 0.03200 | 0.150 | 0.010 | 0.010 |
| C9 | .0105 | 128.259 | 613.31 | 331.99 | 8.7621 | 0.4439 | C9 | 0.120 | 0.03400 | 0.150 | 0.010 | 0.010 |
| C10 | .0073 | 142.286 | 655.07 | 304.15 | 9.6591 | 0.4869 | C10 | 0.120 | 0.03600 | 0.150 | 0.010 | 0.010 |
| C11 | .0049 | 147.000 | 699.91 | 349.54 | 10.172 | 0.4770 | C11 | 0.120 | 0.04300 | 0.150 | 0.010 | 0.010 |
| C12P | .0138 | 210.000 | 797.52 | 324.79 | 14.000 | 0.5266 | C12P | 0.120 | 0.04408 | 0.150 | 0.010 | 0.010 |

In this table, the binary interaction parameters form a zero-trace symmetrical matrix; the boxes comprising a symbol # are filled by symmetry. The missing columns have to be filled on the one hand by the symmetry property, on the other hand by zero binary interaction parameters.

At various depressurization stages distributed between the saturation pressure of the initial fluid and 69 bars, a constant-pressure (the pressure of the stage considered) vaporization operation of the oil phase of the state '$e_d$' considered has been carried out by means of a gas whose composition is considered to be representative of the injection gas during simulation (in the SPE3 case, the composition of the gas injected varies during simulation since it is the gas produced that is reinjected), each vaporization operation comprising several injected gas amount stages until complete vaporization of the liquid phase. A state '$e_{dv}$' corresponds to each injected gas amount stage where the phases are saturated.

Still with the same simulator, the separation operations for the oil and gas phases of each state '$e_d$' and '$e_{dv}$' forming set "E" have been simulated, the separation chain CS_A used comprising a first stage at 26.7° C. and 56.2 bars, a second stage of expansion of the liquid phase from the first separation stage to 26.7° C. and 4.5 bars, and a last expansion of the liquid phase from the second separation stage to 15.6° C. and 1.01325 bars, the gas phases from the various separations being mixed. Since the SPE3 case involves a modification, during simulation, of the pressure conditions of the first separation stage (the pressure changing from 56.2 bars to 21.7 bars), the separation operations of the oil and gas phases of each 'e' state have also been simulated with the other separation chain CS_B.

It has to be noted that the sequence of the various simulation operations described above can be readily carried out with most of the thermodynamic simulation softwares available for industry.

The required conditions described in paragraph d) found from the molar masses of the separation products of the oil and gas phases of each state of set "E" by chains CS_A and CS_B are in gram/mole:

$MM_V \leq 21.592$; $27.865 \leq MM_I \leq 72.334$; $MM_H \geq 162.06$

The molar masses assigned to the three constituents in the BRO representation are given in Table 2.

The three-constituent compositions of the phases of set "E" by the calculations described in paragraphs f) and g) are obtained by considering the separation products of chain CS_A The composition of the initial fluid in the BRO representation is given in Table 2 hereunder:

TABLE 2

SPE3 case - BRO description of the reservoir fluid

| Constituent name | MM | Molar fraction |
|---|---|---|
| V | 21.592 | .856714 |
| I | 62.334 | .092358 |
| H | 162.06 | .050928 |

Phase Properties

The Gibbs rule, which gives the number of degrees of freedom of a thermodynamic system from the number of constituents and the number of phases, applied to a three-constituent mixture, gives three degrees of freedom when two hydrocarbon phases are at equilibrium: the phase properties depend on the pressure, the temperature and a compositional variable.

For each fluid phase for which the phase property values useful for modelling the flows (compressibility factor, viscosity, . . . ) are known for given pressure and temperature conditions, these phase properties can be entered in form of tables which are a function of the pressure, the temperature, and an index of the composition in the three-constituent representation. This data can be used afterwards as input data in a simulator, the simulator generally having internal interpolation or extrapolation methods for estimating the phase properties at intermediate points.

k) Alternatively to the use of tables, it is possible to seek, for example by regression, the correlation or state equation parameters allowing to calculate, by thermodynamic zone, the properties of the phases as a function of the composition and the pressure and temperature conditions, these parameters being then introduced in the simulation model instead of the tables described above.

A reliable state equation for the reservoir fluid described in detail in the base representation is frequently available.

Thus, when a state equation (and an associated correlation for viscosity calculation) defined for the detailed $N_{rb}$-constituent representation allows to model the thermodynamic behaviour of the fluids during the pressure and temperature stages of a thermodynamic path followed in one or more thermodynamic zones, this state equation can be used to generate the reference set of the compositions of fluids and the aforementioned properties of the corresponding phases, by adding thereto the parameters of the phases in the state equation, such as the covolume, the attraction term, the critical pressure, . . . , which can be considered to be specific properties of the phases. For each fluid composition obtained, the same state equation, or another one, can be used to generate the compositions and properties of the fluid mixtures produced by a separation chain, and thus allow application of the pseudoisation method described in paragraphs a) to i).

When the parameters of the pseudo-components in a state equation, and in a correlation for viscosity calculation, are adjusted, for example by regression, to reproduce the specific properties of the phases such as the covolume, the attraction term, the critical temperature, . . . , obtained with the detailed representation, we obtain a state equation and a correlation that can be used for calculation of the phase properties such as the compressibility factor, the viscosity, but this first state equation, referred to hereafter in short form as EOS_PRO, is not necessarily valid for the equilibrium calculations notably if the observance of a condition of equality of the fugacities at equilibrium has not been taken into account.

A non limitative procedure allowing to obtain the parameters of the state equation EOS_PRO of the BRO representation is the procedure followed for the 'SPE3' case presented by way of illustration. The state equation used, the Peng-Robinson equation, is reminded hereafter for better understanding of the approach, but the procedure can be readily applied to other state equations.

l) The Peng-Robinson equation is written as follows for phase P:

$$P = \frac{RT}{V_p - b_p} - \frac{a(T)_p}{(V_p + b_p)^2 - 2b_p^2} \quad (15)$$

where R is the perfect gas constant, T the temperature, P the pressure, V the molar volume of phase P, b its covolume and a(T) its attraction term, the latter quantities being expressed by:

$$b_P = \sum_i c_i b_i \qquad (16)$$

$$a(T)_P = \sum_j c_j \left[\sum_i c_i a_{ij}(T)\right] avec\ a_{ij}(T) = \sqrt{a_i(T)}\sqrt{a_j(T)}(1-\delta_{ij}) \qquad (17)$$

where $c_i$ denotes the molar fraction of constituent i in phase P, a molar fraction whose physical dependences are omitted to lighten the presentation, $b_i$ and $a_i(T)$ respectively the covolume and the attraction term of constituent i, $\delta_{ij}$ the parameter of binary attraction between constituents i and j, the $\delta_{ij}$ forming a zero-trace symmetrical matrix.

In dimensionless form, the Peng-Robinson equation is expressed as follows:

$$Z_P^3 - (1-B_P)Z_P^2 + (A_P - 3B_P^2 - 2B_P)Z_P - (A_P B_P - B_P^2 B_P^3) = 0 \qquad (18)$$

where Z is the compressibility factor of phase P, B and A are the dimensionless forms of the covolume and the attraction term of phase P (the dependences of the variables with the pressure and temperature being omitted to lighten writing of the equations):

$$B_p = b_p \frac{P}{RT} \qquad (19)$$

$$A_p = a_p \frac{P}{R^2 T^2} \qquad (20)$$

m) The compressibility factor of phase P is only a function of the two dimensionless phase parameters A and B. It follows therefrom that estimation of the parameters per constituent in the BRO representation (i.e. $b_V$, $b_I$, $b_H$, $a_V(T)$, $a_I(T)$, $a_H(T)$, $\delta_{VI}$, $\delta_{VH}$, $\delta_{IH}$) allowing to reproduce the values of a(T) and b, obtained for each phase at the various stages of the PVT simulations with the base representation (detailed with 16 constituents), allows to reproduce the reference values of the compressibility factors of the phases. The regression procedure used to obtain the various parameters of the BRO representation is the minimization of objective functions of the form:

$$O(\vec{p}) = \sum_e^{e \in E} \varpi_G^e [\varphi_G^e(\vec{p}) - 0_G^e]^2 + \sum_e^{e \in E} \varpi_o^e [\varphi_o^e(\vec{p}) - o_o^e]^2 \qquad (21)$$

where the observable quantity o per phase and per state e, obtained here with the detailed 16-constituent representation, is modelled by a functional $\phi$ parameterized by the components $p_x$ of vector $\vec{p}$, and where quantities $\varpi$ are weights assigned to the various observables.

The minimum of $O(\vec{p})$ is obtained by solving the system of equations, of same dimension as vector $\vec{p}$, formed by the nullity of the partial derivatives of function $O(\vec{p})$ with respect to the various parameters $p_x$:

$$\partial_{p_x} O(\vec{p}) = 0 \qquad (22)$$

i.e.:

$$\sum_e^{e \in E} \varpi_G^e [\varphi_G^e(\vec{p}) - o_G^e]^2 \partial_{p_x} \varphi_G^e(\vec{p}) + \sum_e^{e \in E} \varpi_O^e [\varphi_O^e(\vec{p}) - o_O^e] \partial_{p_x} \varphi_O^e(\vec{p}) = 0 \qquad (23)$$

n) When seeking the values of parameters $b_K$ (K=V,I,H) of the BRO representation, the objective function used in the SPE3 case is thus:

$$O(b_V, b_I, b_H) = \qquad (24)$$

$$\sum_e^{e \in E} \varpi_G^e \left[\sum_K y_K^e b_K - b_G^e\right]^2 + \sum_e^{e \in E} \varpi_O^e \left[\sum_K x_K^e b_K - b_O^e\right]^2$$

The system to be solved is simply a linear system of three equations in three unknowns:

$$\begin{cases} m_{VV} b_V + m_{VI} b_I + m_{VH} b_H = r_V \\ m_{IV} b_V + m_{II} b_I + m_{IH} b_H = r_I \\ m_{HV} b_V + m_{HI} b_I + m_{HH} b_H = r_H \end{cases} \qquad (25)$$

the terms $m_{KK'}$ and $r_K$ of the second members of the equations being given by:

$$m_{KK'} = \sum_e^{e \in E} (\varpi_G^e y_K^e y_{K'}^e + \varpi_O^e x_K^e x_{K'}^e); \quad r_K = \sum_e^{e \in E} (\varpi_O^e x_K^e b_O^e + \varpi_G^e y_K^e b_G^e)$$

o) In order to seek parameters $a_V(T)$, $a_I(T)$, $a_H(T)$, $\delta_{VI}$, $\delta_{VH}$, $\delta_{IH}$ simply by solution of linear systems of three equations in three unknowns, equation (17) can be rewritten as the sum of two terms, the second term comprising the binary interactions:

$$a(T)_P = a_1(T)P^2 + a_2(T)P \qquad (26)$$

with:

$$a_1(T)_p = \sum_i c_i \sqrt{a_i(T)} \text{ and } a_2(T)_p = \qquad (27)$$

$$-\sum_j \sum_i c_j c_i \alpha_{ij} o\grave{u} a_{ij}(T) = \sqrt{a_i(T)}\sqrt{a_j(T)}\delta_{ij}$$

In term $a_2(T)_P$, parameters $\alpha_{ij}(T)$ form a set of three independent parameters $\alpha_{VI}(T)$, $\alpha_{VH}(T)$, $\alpha_{IH}(T)$.

Using terms $a_1(T)$, obtained during the PVT simulations with the detailed 16-constituent representation, as observable quantities o per phase and per state, the unknowns being quantities $\sqrt{a_V(T)}$, $\sqrt{a_I(T)}$, $\sqrt{a_H(T)}$, the problem to be solved is actually similar to the problem described to obtain the covolume parameters of the constituents of the BRO representation. Similarly, parameters $\alpha_{ij}(T)$ are obtained by solving the system of three equations in three unknowns formed from observable quantities $a_2(T)$.

p) The binary interaction parameters can then be obtained by:

$$\delta_{VI} = \frac{\alpha_{VI}(T)}{\sqrt{a_V(T)}\sqrt{a_I(T)}}, \quad (28)$$

$$\delta_{VH} = \frac{\alpha_{VH}(T)}{\sqrt{a_V(T)}\sqrt{a_H(T)}}; \delta_{IH} = \frac{\alpha_{IH}(T)}{\sqrt{a_I(T)}\sqrt{a_H(T)}}$$

q) Some simulators accept, as parameters of the constituents for the state equation, direct introduction of the covolumes $b_i$ of the constituents and of the matrix of parameters $a_{ij}(T)$ involved in the calculation of the attraction term (see equation (17)), and this matrix has to be defined if need be for different temperatures.

If the case treated requires a temperature dependence (variable temperature in the reservoir), the previous procedure can be adapted, for example by generating set "E" by PVT operations at various reservoir temperatures, considering states e at various temperatures to obtain the covolumes per constituent (which have to be the same for the different temperatures), considering the states e obtained at a given temperature to, generate the corresponding matrix of parameters $a_{ij}(T^e)$ and by repeating the procedure for as many temperatures T as necessary.

r) When the simulator does not accept direct introduction of the covolume per constituent $b_i$ and of the matrices of parameters $a_{ij}(T^e)$:

the covolume per constituent is generally obtained from the introduction of parameters $Tc_i$, $Pc_i$, optionally $\Omega b_i$ (by default all equal to 0.077796) by:

$$b_i = R\Omega b_i \frac{Tc_i}{Pc_i} \quad (29)$$

quantities $a_i(T)$ are generally obtained by:

$$\sqrt{a_i(T)} = \sqrt{a0_i}\left[1 + \zeta_i\left(1 - \sqrt{\frac{T}{Tc_i}}\right)\right] \text{ with } \zeta_i = \sum_{n=0}^{dp} C_n \omega_i^n \quad (30)$$

Quantity $a0_i$ is generally obtained from the introduction of parameters $Tc_i$, $Pc_i$, optionally $\Omega a_i$ (by default all equal to 0.457235) by:

$$a0_i = R^2\Omega a_i \frac{Tc_i^2}{Pc_i} \quad (31)$$

In polynomial $\zeta_i$ of degree dp, parameters $\omega_i$ are the acentric factors of the constituents generally considered to be constant, and the degree of the polynomial and constants $C_n$ can vary from one simulator to the next.

s) When the critical pressures, temperatures and volumes per constituent are required, the critical pressures, temperatures and volumes of the phases of set "E", defined by mixture laws identical to those used for the covolumes, can be used as observables:

$$Pc_p = \sum_i c_i Pc_i; \quad Tc_p = \sum_i c_i Tc_i; \quad Vc_p = \sum_i c_i Vc_i \quad (32)$$

Parameters $Pc_V$, $Pc_I$, $Pc_H$, $Tc_V$, $Tc_I$, $Tc_H$ and $Vc_V$, $Vc_I$, $Vc_H$ respectively can thus be obtained by successive solution of three systems of equations in three unknowns totally similar to those generated for calculation of the covolumes per constituent, developed above.

t) Parameters $\Omega b_K$ (K=V,I,H) are then obtained from equation (29) and parameters $b_K$, $Pc_K$ and $Tc_K$ as determined in paragraphs n) and s), by:

$$\Omega b_K = \frac{Pc_K b_K}{R Tc_K} \quad (33)$$

u) In equation (30), in the most frequent case where the reservoir temperature is considered to be constant, the temperature dependence of quantities $\sqrt{a_V(T)}$, $\sqrt{a_I(T)}$, $\sqrt{a_H(T)}$ can be disregarded by selecting a zero value for the acentric factors of constituents V, I, H, hence:

$$\sqrt{a_K(T)} \equiv \sqrt{a0_K}, \forall K, K=V,I,H \quad (34)$$

and parameters $\Omega a_K$ (K=V,I,H) are then obtained from parameters $\sqrt{a_K(T)}$, $Pc_K$ and $Tc_K$ as determined in paragraphs o) and s), by:

$$\Omega a_K = \frac{Pc_K a_K(T)}{R^2 Tc_K^2} \quad (35)$$

Another possibility, used in the SPE3 case, consists in assigning to parameters $\Omega a_K$ (K=V,I,H) a value by default. In this case, parameters $\sqrt{a0_K}$ are determined with the $Pc_K$ and $Tc_K$ as determined in paragraph s), and parameters $\zeta_K$ are then obtained by rearranging equation (30):

$$\zeta_K = \frac{\frac{\sqrt{a_K(T)}}{\sqrt{a0_K}} - 1}{1 - \sqrt{\frac{T}{Tc_K}}} \quad (36)$$

then acentric factors $\omega_K$ are sought as solutions to the three polynomial equations (K=V,I,H):

$$\sum_{n=0}^{dp} C_n \omega_K^n - \zeta_K = 0 \quad (37)$$

v) When, for the case considered, the reservoir temperature is variable, equation (30) can be rewritten as follows:

$$\sqrt{a_K(T^e)} = \beta_K + \gamma_K \eta_K(T^e) \quad (38)$$

with the quantities:

$$\eta_K(T^e) = 1 - \sqrt{\frac{T^e}{Tc_K}}$$

calculated using the critical temperatures of the constituents as determined in paragraph s).

We can then seek quantities $\beta_K$ and $\gamma_K$ ($\beta_K = \sqrt{a0_K}$ and $\gamma_K = \sqrt{a_K \zeta_K}$) as independent parameters by linear regression of the pairs of values $\eta_K(T^e)$, $\sqrt{a_K(T^e)}$, the latter values being determined in paragraphs o) and q).

Parameters $\Omega a_K$ and $\zeta_K$ are then obtained by:

$$\Omega a_K = \frac{Pc_K \beta_K^2}{R^2 Tc_K^2} \text{ and } \zeta_K = \frac{\gamma_K}{\beta_K} \tag{39}$$

The acentric factors sought are solutions to the three polynomial equations (K=V,I,H):

$$\sum_{n=0}^{dp} C_n \omega_K^n - \frac{\gamma_K}{\beta_K} = 0 \tag{40}$$

w) Volume correction factors are often used to adjust the phase densities. When volume correction factors per constituent are required, it is possible to use as observable quantities the volume corrections of the phases of set "E", defined by mixture laws identical to those used for the covolumes:

$$Cv_P = \sum_i c_i Cv_i \tag{41}$$

Parameters $Cv_V$, $Cv_I$, $Cv_H$ can then be obtained by solving a system of three equations in three unknowns totally similar to the system generated for calculation of the covolumes per constituent developed in paragraph n).

x) In the SPE3 case, the hydrocarbon phase viscosity calculations are carried out with a correlation widely used in the field of petroleum engineering, the Lohrenz, John, Bray, B. G. and Clark, C. R. correlation: "Calculating Viscosities of Reservoir Fluids from their Compositions", Journal of Petroleum Technology, 1964, pp. 1171-1176. The phase parameters explicitly used in this correlation are the critical pressures, temperatures, volumes of the phases. Determination of the critical parameters (pressure, temperature, volume) of constituents V, I, H as described in paragraph s) has allowed suitable modelling of the phase viscosities with the BRO representation. The procedure can be readily applied to other correlations.

y) The guiding line followed throughout paragraphs n) to w) consists in seeking the state equation parameters EOS_PRO useful for calculation, under the reservoir conditions, of the phase densities (via the compressibility factors) and of the viscosities by simple solutions (non iterative) of systems of linear equations.

Figure 6:
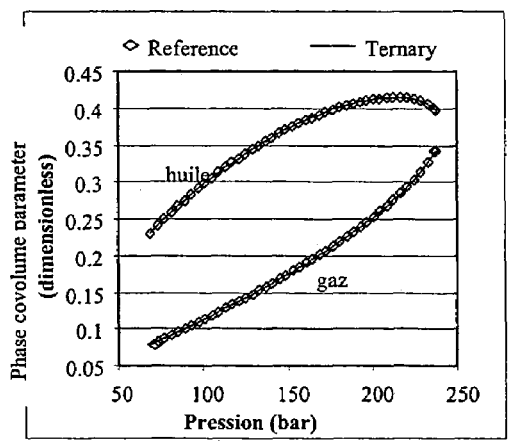
Figure 7A:
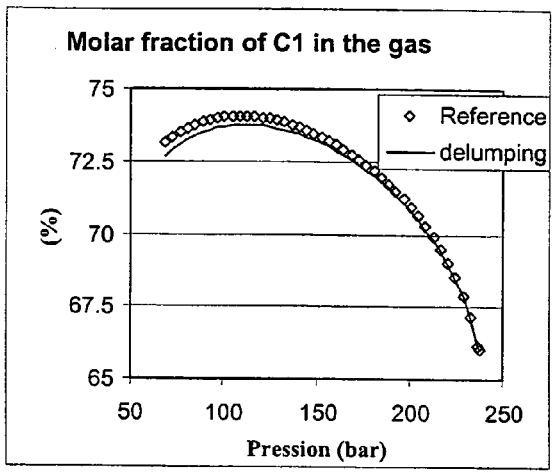
Figure 8A:
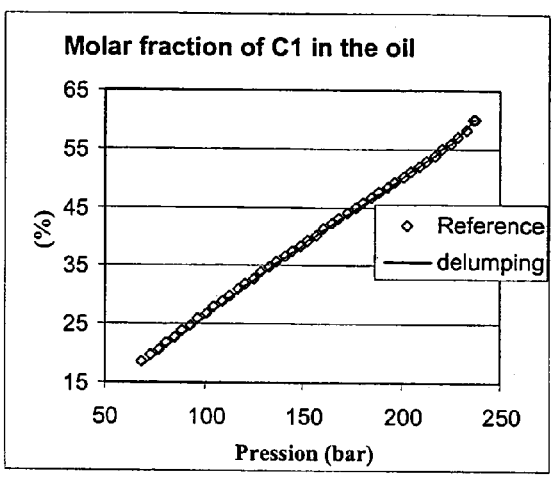
Figure 7B:
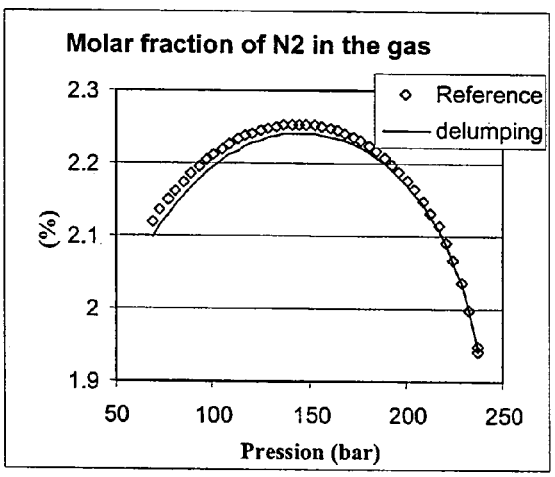
Figure 8B:
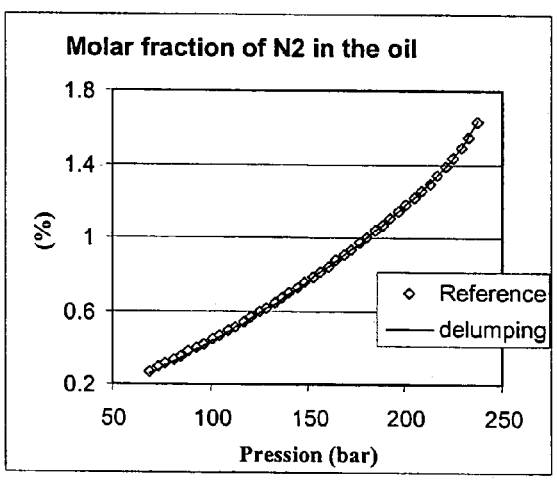
Figure 7C:
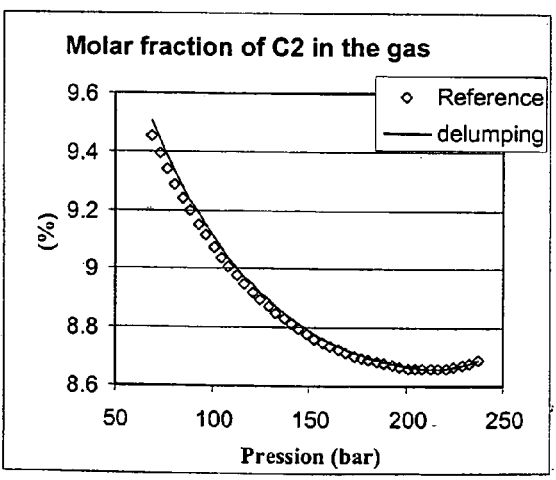
Figure 8C:
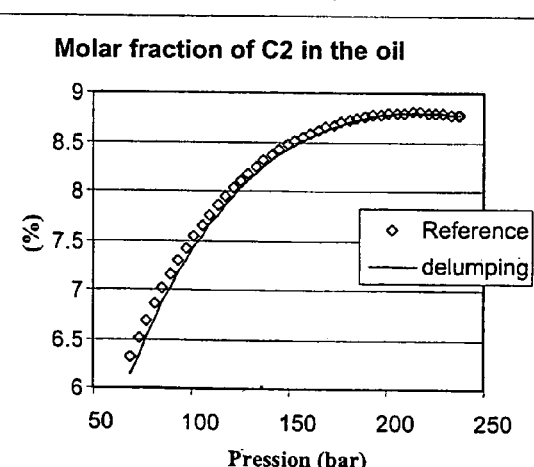
Figure 7D:
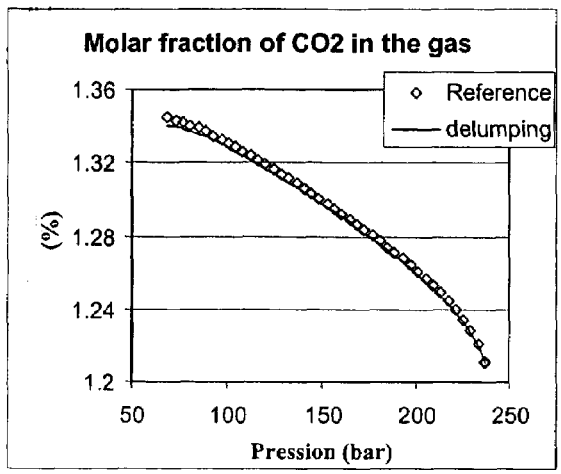
Figure 8D:
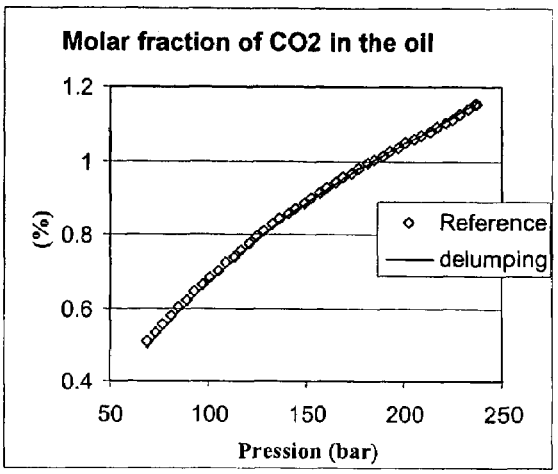
Figure 7E:
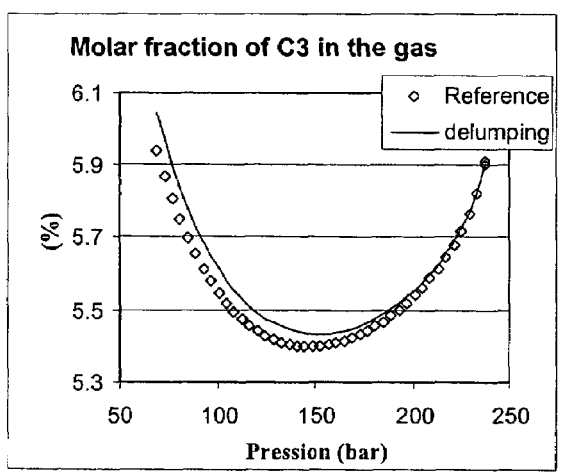
Figure 8E:
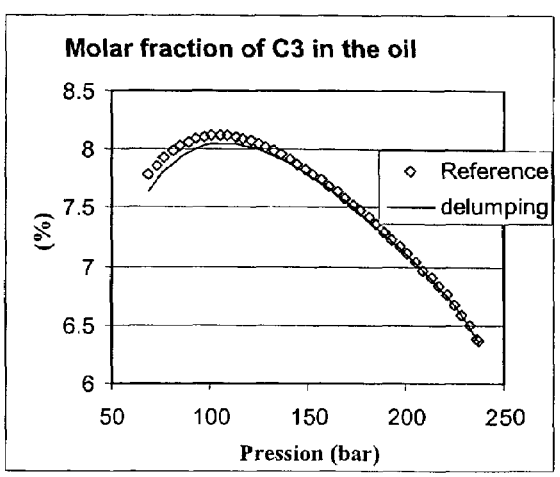
Figure 7F:
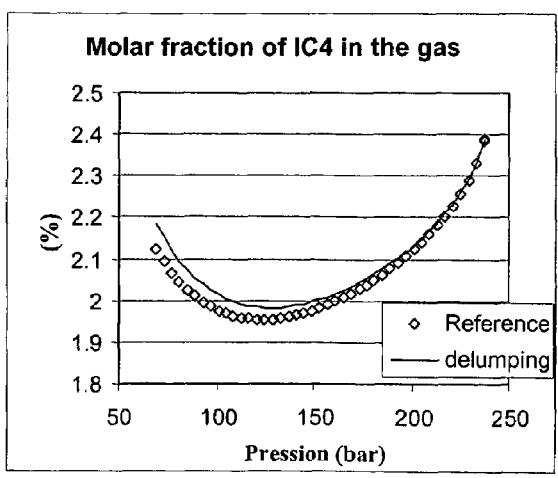
Figure 8F:
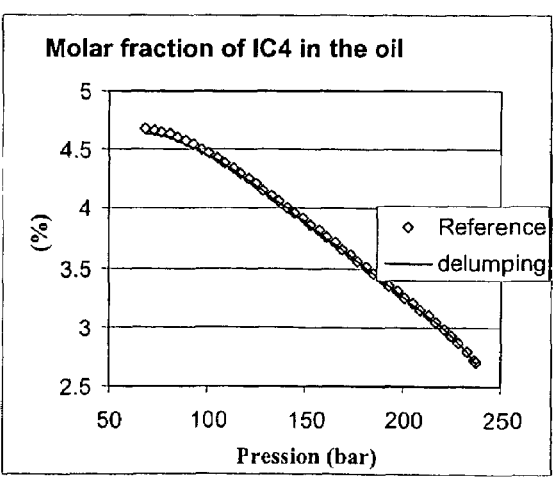
Figure 7G:
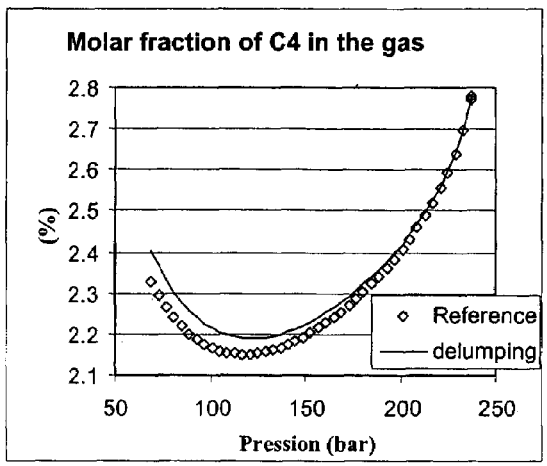
Figure 8G:
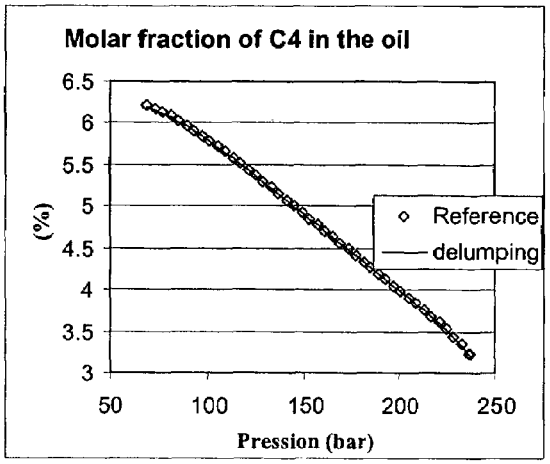
Figure 7H:
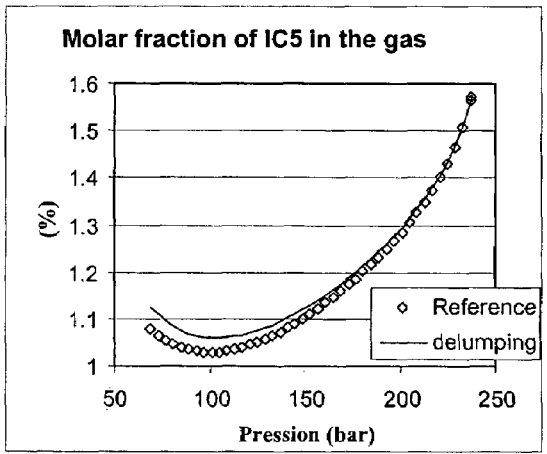
Figure 8H:
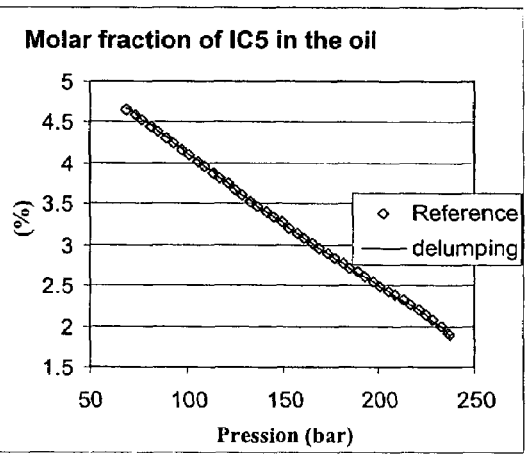
Figure 7I:
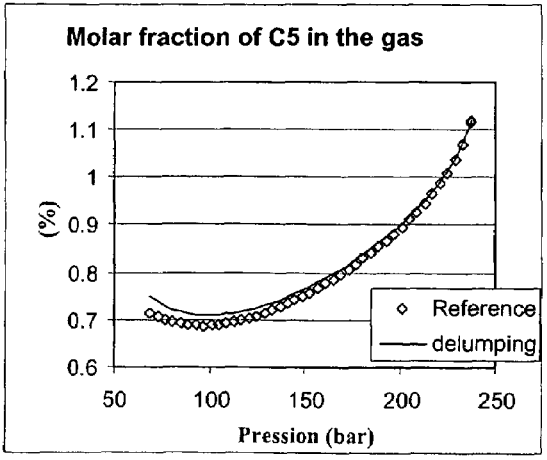
Figure 8I:
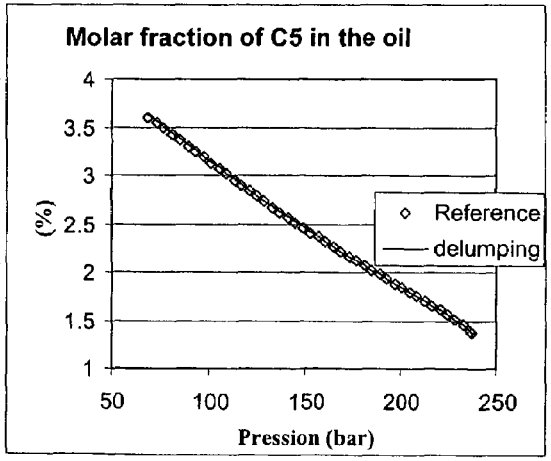
Figure 7J:
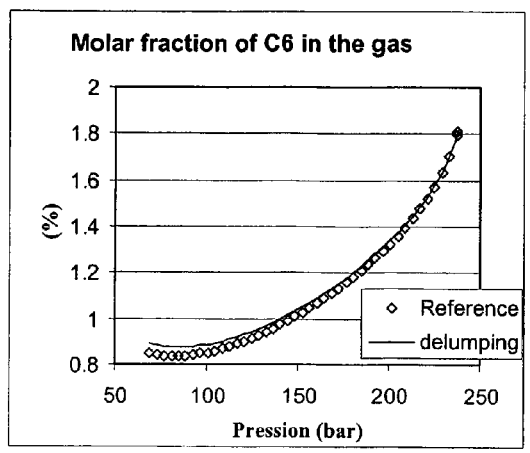
Figure 8J:
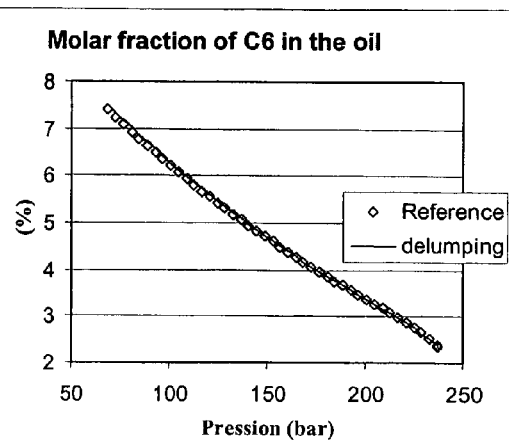
Figure 7K:
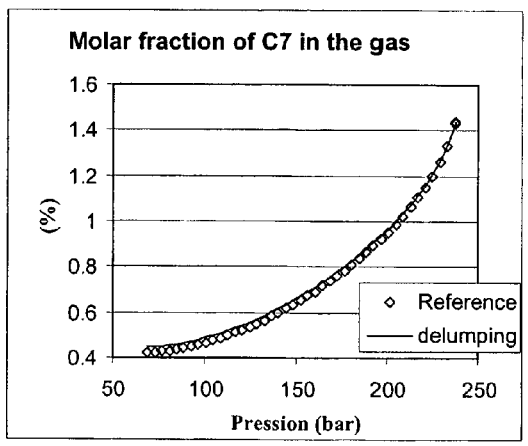
Figure 8K:
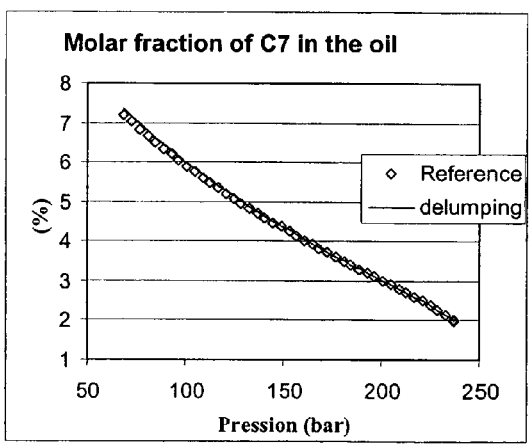
Figure 7L:
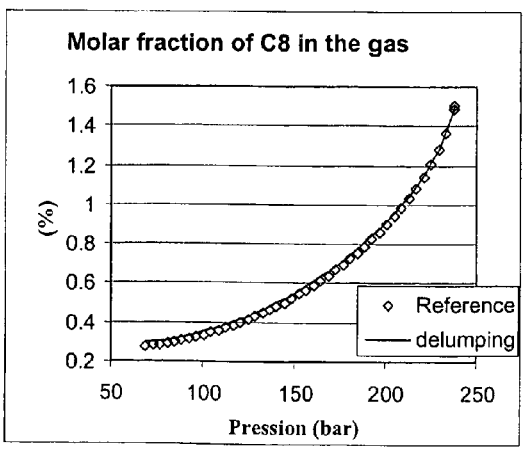
Figure 8L:
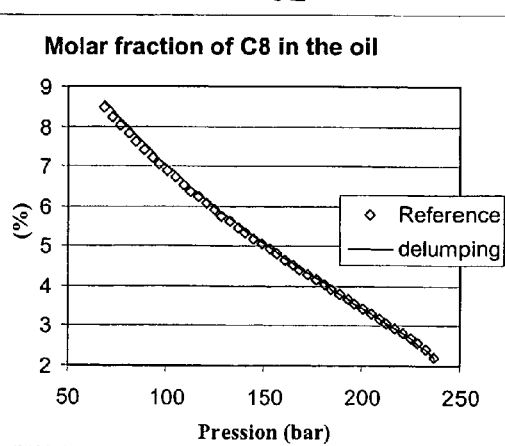
Figure 7M:
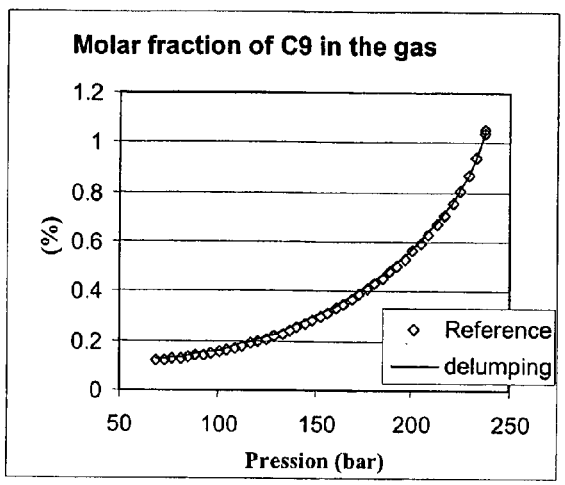
Figure 8M:
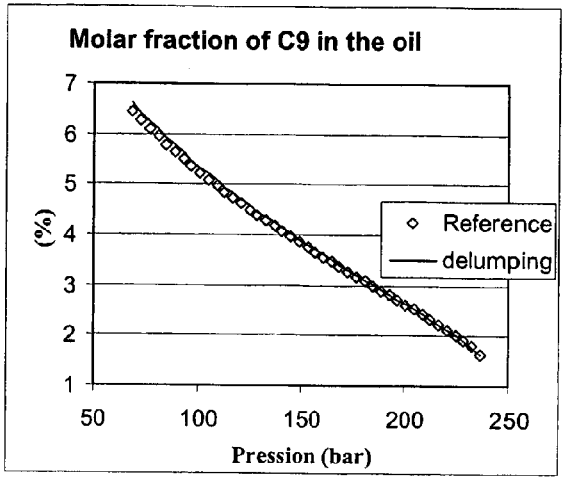
Figure 7N:
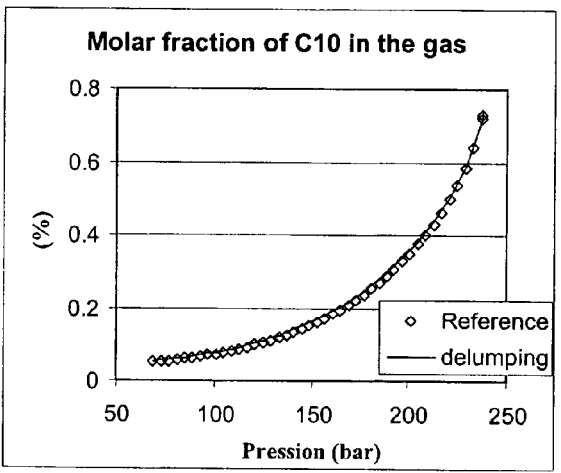
Figure 8N:
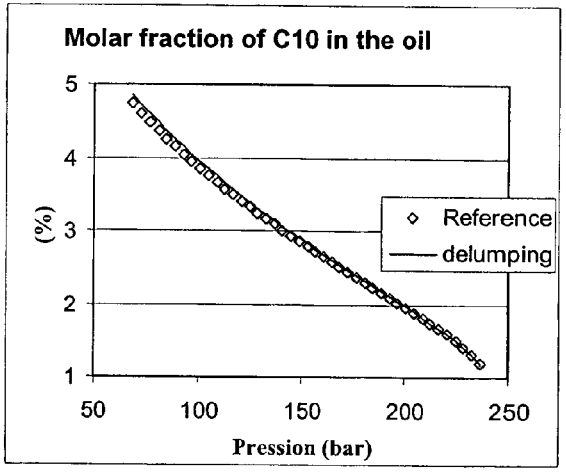
Figure 7O:
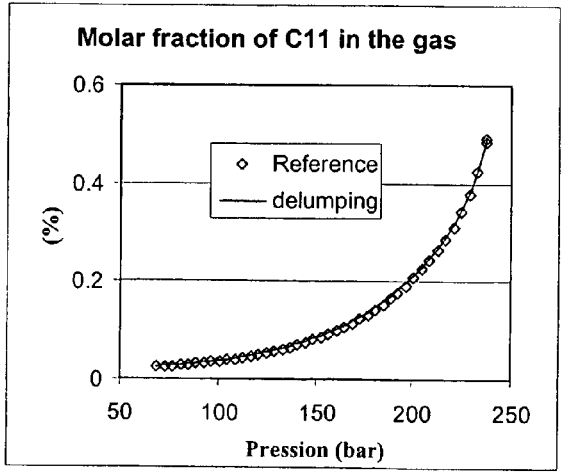
Figure 8O:
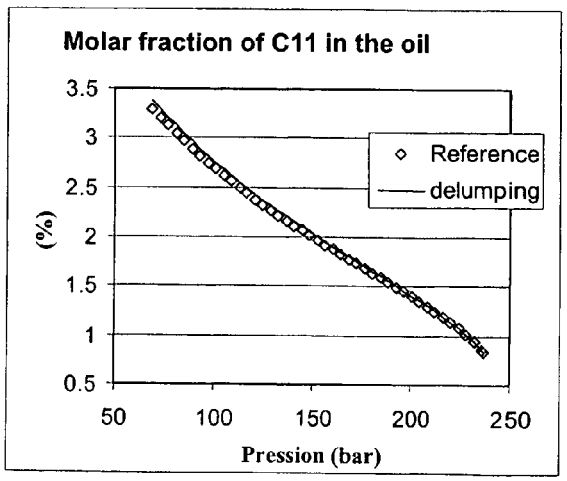
Figure 7P:
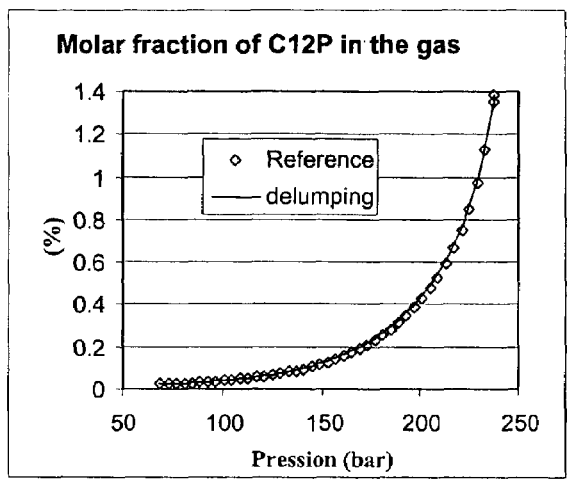
Figure 8P:
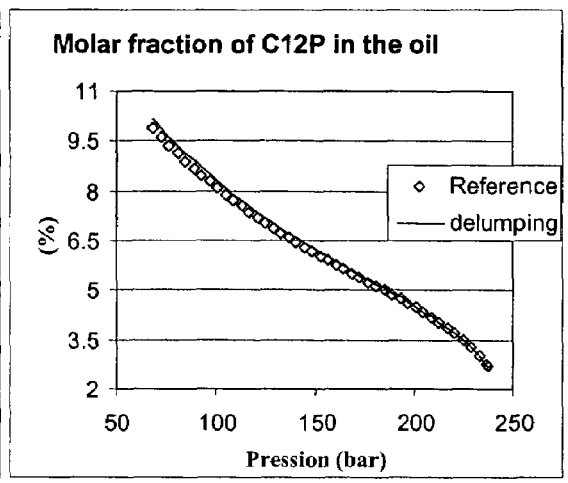

Its efficiency in reproducing the covolumes and attraction terms of the phases is illustrated, for the fluids of the SPE3 case, by FIGS. 6 and 7 for a depressurization operation at constant volume at the reservoir temperature (93.33° C.) from the dew-point pressure bars of the initial reservoir fluid (237.4 bars) to 69 bars. Each figure shows the quantities calculated from the state equation of the detailed reference representation and the quantities calculated from the state equation EOS_PRO of the BRO model, these quantities practically merging with one another.

This same line has been successfully used for treating other cases that are not described here. It has been observed that such a line can be widely adapted to variable temperature contexts. Besides, the necessary processings pose no particular coding problems and have been easily automated.

The parameters of the EOS_PRO used for the SPE3 case illustrated are given in Table 3 hereunder:

TABLE 3

SPE3 case - Parameters of the EOS_PRO of the BRO representation

| Name | $T_c$ ° F. | $P_c$ psi | $V_c$ ft³/lbm | $\omega$ | $\Omega b$ | Cv ft³/lbm | $\delta_{KK'}$ | V | I | H |
|---|---|---|---|---|---|---|---|---|---|---|
| V | −61.212 | 666.02 | 1.869 | −0.02043 | 0.079345 | −0.0686 | V | 0.0 | 0.058447 | 0.002065 |
| I | 368.292 | 581.21 | 4.389 | 0.31255 | 0.082877 | −0.0621 | I | # | 0.000000 | 0.001604 |
| H | 663.138 | 263.46 | 10.99 | 0.21233 | 0.065003 | 0.2664 | H | # | # | 0.000000 | z) In the SPE3 case, we have chosen to use for the EOS_PRO a state equation of the same type as the equation used for the base representation. This is not obligatory. It is possible to use a state equation of another type, from the moment that this other state equation uses phase parameters identifiable with the phase parameters used by the reference state equation.

More generally the parameters required for the BRO representation can be obtained by various techniques known as regression, inversion, optimization, . . . , that can be found in an extensive literary output. They can for example be sought by means of one or more iterative solutions of systems of equations formed by partial derivatives, in relation to subsets or to the set of parameters of the BRO representation, of an objective function of the type of equation (21) or of another type.

We could even try to use a formalism of this type to optimize one or more of the molar masses of constituents V, I, H by using it (or them) explicitly—by replacement in the objective function of the phase compositions by their expressions given by equations (8) and (9)—, and by selecting observable quantities sensitive to their value(s). Such an approach could be considered in a situation, which has not been encountered so far, where the guiding line followed throughout paragraphs n) to w) leads to a determination of the BRO representation parameters that does not allow accurate reproduction of the observable quantities.

Finally, for reasons known per se, one may be led to give a priori values to some of the parameters of the EOS_PRO equation and then to carry out estimation calculations only for a limited number of parameters.

aa) The first expression generally expected from the simulation results are volume results. The observables which then have to be reproduced are the molar volumes of the phases after separation. For the SPE3 case, we used two distinct correlations, one for calculation of the molar volumes of the gas phases at the separation outlet, the other for molar calculation of the oil phases at the separation outlet, the separation outlet conditions being the standard conditions used in the profession, i.e. an atmosphere at 15.56° C. (60° F.).

Many correlations or state equations are available for estimating the molar volume of a gas phase, notably under conditions close to atmospheric conditions. For information, it is the P. M. Dranchuk and J. H. Abou-Kassem correlation (presented in the paper: "Calculating Z Factors for Natural Gases using Equations of State", JCPT, July-September 1975) that has been used for the SPE3 case where the parameters useful for calculation of the molar volume of the gas are the critical pressures and temperatures of constituents (V) and (I), parameters which have been subjected to an iterative regression so as to reproduce the molar volumes of the gas phases obtained by the PVT separation simulations with the 16-constituent representation.

The variation, as a function of the molar fraction of constituent I, of the molar volume of the oil phases under conditions close to atmospheric conditions has been found, in the SPE3 case, practically linear, more generally, for cases that are not described here, representable by a polynomial of low degree (degree two to three). For the SPE3 case, it is a linear dependence that has been selected, whose parameters are obtained by simple linear regression.

The parameters required for calculation of the molar volumes under separation conditions were obtained for the two separation chains CS_A and CS_B with the same method.

Thermodynamic Equilibria bb) The equilibrium calculations can be carried out either from equilibrium coefficient data, or from the expression of the equality of the fugacities of all the constituents in each phase, these two options being respectively presented hereafter.

cc) According to Gibbs' rule, for calculation of the equilibria in the reservoir, the equilibrium coefficients of pseudo-components (V), (I), (H) as, calculated by the set of equations (10) can be introduced in tables as functions of the pressure, temperature, and of an index of the composition in the pseudo-representation. This data can then be used as input data in a simulator, the simulator generally having internal interpolation or extrapolation methods for estimating the equilibrium coefficients at intermediate points. It is also possible, prior to introducing the data in a simulator, to add points to the tables using interpolation or extrapolation methods known in the art, or to use, instead of the tables, correlations constructed to reproduce the equilibrium coefficients.

A dependence of the equilibrium coefficients with the pressure, the temperature and the composition index is not always necessary. Thus, in many application cases, one may be led to leave out the dependence with respect to a compositional index. These cases, where the number of degrees of freedom of the equilibrium coefficients would be reduced, remain within the scope of the method provided.

dd) For calculation of the equilibria at the end of a separation chain, the equilibrium coefficients of pseudo-components (V) and (H) are respectively infinite and zero, whatever the pressure and temperature conditions at the separation chain outlet and whatever the composition of the mixture subjected to separation. If need be, in a simulator that may not accept the concept of infinite or zero equilibrium coefficients (this concept being often implemented by forcing the absence of the constituent respectively in the oil phase and in the gas phase), it is possible to use a very great finite value and a very low finite value, both positive, instead of infinite or zero equilibrium coefficients. For the data relative to the equilibrium coefficients of constituent (I) necessary for equilibrium calculation, the set of equations (11) gives a different definition of the equilibrium coefficients of constituent (I) according to whether the separation of a 'gas' phase from the reservoir or the separation of an 'oil' phase from the reservoir is considered. The input data, in principle necessary for equilibrium calculations, is thus, per phase, a table of equilibrium coefficients of constituent (I) as a function of a compositional index of the phase subjected to separation, of the pressure and of the temperature at the outlet of the separation chain considered. The variation ranges of the compositions of the oil and gas phases being generally distinct, it may be convenient to "merge" into a single table the data useful for the oil and gas phases, notably if the simulator does not accept introduction of distinct data for each phase.

This data can be used as input data in a simulator, the simulator generally having internal interpolation or extrapolation methods for estimating the equilibrium coefficients at intermediate points. It is also possible, prior to introducing the data in a simulator, to add points to the tables using interpolation or extrapolation methods known in the art, or to use, instead of the tables, correlations constructed to reproduce the equilibrium coefficients.

ee) If the EOS_PRO state equation is constructed to reproduce the phase properties, it is not necessarily valid for equilibrium calculations, i.e. to allow reproduction of the compositions of the phases of set "E" obtained in paragraph g). As above, the Peng-Robinson equation is used hereafter as presentation support.

For this state equation, the equilibrium coefficients, according to the condition of equality of the fugacities of each constituent in each phase at equilibrium, are obtained by:

$$Ln(K_i) = D_0 + D_1 b_i + \frac{P}{\sqrt{2} R^2 T^2} \sum_{j=1}^{N} \left(\frac{L_G}{B_G} y_j - \frac{L_O}{B_O} x_j\right) a_{ij}(T) \quad (42)$$

with the dimensionless phase parameters defined according to equations (19) and (20) and:

$$\begin{cases} L_P = Ln\left(\frac{Z_P + (1+\sqrt{2})B_P}{Z_P + (1-\sqrt{2})B_P}\right) \\ D_0 = Ln\left(\frac{Z_G - B_G}{Z_O - B_O}\right) \\ D_1 = \frac{P}{RT}\left[\frac{Z_O - 1}{B_O} - \frac{Z_G - 1}{B_G} + \frac{A_O L_O}{2\sqrt{2} B_O^2} - \frac{A_G L_G}{2\sqrt{2} B_G^2}\right] \end{cases} \quad (43)$$

and the compressibility factors of the phases calculated from equation (18).

For a case where the reservoir temperature is constant, the problem consists in determining the nine independent parameters forming a vector $\bar{p}$: $b_v$, $b_I$, $b_H$, $a_{VV}$, $a_{II}$, $a_{HH}$, $a_{VI}$, $a_{VH}$, $a_{IH}$, for example by minimizing an object function constructed using as observables $O_K^e$ the equilibrium coefficients of set "E" as calculated by equations (10). The objective function according to equation (21) can then be adapted as:

$$O(\vec{p}) = \sum_{e}^{e \in E} \sum_{K=V,I,H} \varpi_K^e \left[\varphi_K^e(\vec{p}) - o_K^e\right]^2 \quad (44)$$

where functions $\phi_K^e(\vec{p})$ are the exponentials of the second members of equations (42).

Alternatively, in equation (44), we could use as observables $O_K^e$ the logarithms of the equilibrium coefficients of set "E" and as functions $\phi_K^e(\vec{p})$ the second members of equation (42).

By following K. E. Starling's procedure in the paper: "A New Approach for Determining Equation-of-State Parameters Using Phase Equilibria Data", SPE 1481, SPEJ, December 1966, we can select weights $\omega_K^e$ as the inverses of the values of observables $O_K^e$.

The nullity of the partial derivatives of function $O(\vec{p})$ with respect to the nine parameters of interest-provides a system of nine non-linear equations in nine unknowns, that can be solved iteratively only, many methods suited to solution of non-linear systems being discussed in the literature.

An iterative calculation of this type requires a first approximation of the parameters vector. It has been observed, notably for the SPE3 case, that it is appropriate to profit from the parameters obtained for the EOS_PRO to start the iterative calculations.

More generally, notably to reproduce equilibrium coefficients at various temperatures, we can consider another set or subset of parameters for vector $\vec{p}$ and other parameter seek techniques.

ff) By way of illustration, for the SPE3 case, vector $\vec{p}$ consists of the six parameters $PC_K$ and $\Omega b_k$, the values of the other parameters being taken from equation EOS_PRO. The procedure used for the SPE3 case is a procedure known in the art that is being improved. The set of parameters EOS_EQ used for the SPE3 case is given in Table 4 hereafter:

TABLE 4

SPE3 case - Parameters of the EOS_EQ of the BRO representation

| Name | $T_c$ ° F. | $P_c$ psi | $\omega$ | $\Omega b$ | $\delta_{KK'}$ | V | I | H |
|---|---|---|---|---|---|---|---|---|
| V | −61.212 | 848.47 | −0.02043 | 0.089345 | V | 0.0 | 0.058447 | 0.002065 |
| I | 368.292 | 274.23 | 0.31255 | 0.070000 | I | # | 0.000000 | 0.001604 |
| H | 663.138 | 309.90 | 0.21233 | 0.065003 | H | # | # | 0.000000 | gg) In the SPE3 case, the data introduced for the surface equilibrium calculations for each separation chain CS_A and CS_B are the equilibrium coefficients of constituent (I) in form of a single table for the separation of the oil and gas phases, a table obtained as described in paragraph dd) with, as the single abscissa, the index of the composition of the phase before separation.

hh) FIGS. 1 to 4 compare the results, over the fifteen simulated years of production of the SPE3 case, of a compositional simulation with three pseudo-components BRO (results referred to as 'ternary'), where the compositional representation was obtained by applying the method according to the invention, with those of a detailed compositional simulation with sixteen base constituents (results referred to as 'reference').

The reference compositional simulation uses the same Peng-Robinson state equation for the equilibrium calculations and for the phase property calculations, and for all the thermodynamic zones. The three-constituent BRO simulation uses, for calculation in the reservoir grids, state equation (EOS_EQ) for the equilibrium calculations and state equation (EOS_PRO) for the phase property calculations. For the surface condition calculations, the BRO simulation uses equilibrium coefficients introduced in form of tables and simple correlations for calculation of the phase volumes.

Figure 4:
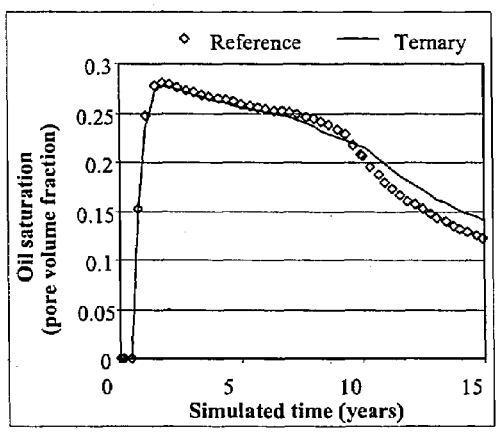

The results shown in FIG. 1, which represent the evolution of the pressure at the bottom of a producing well, and in FIG. 4, which represent the oil (or condensate) saturation evolution in the deepest perforated grid in the producing well, are among the most revealing results of the right calculation of the equilibria and phase properties in the in situ conditions.

Figure 2:
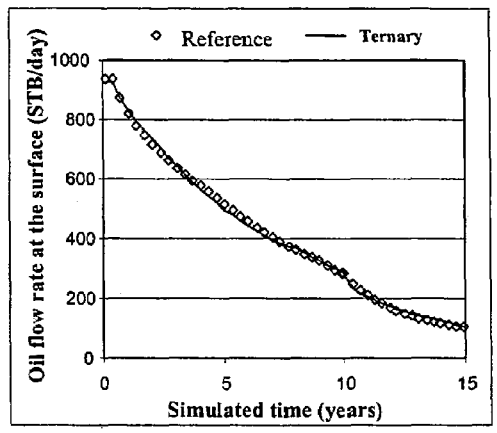
Figure 3:
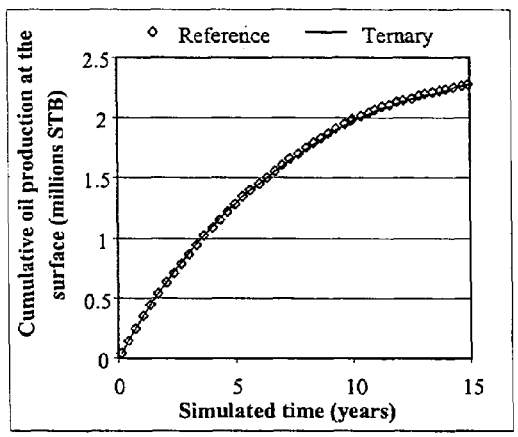
Figure 5:
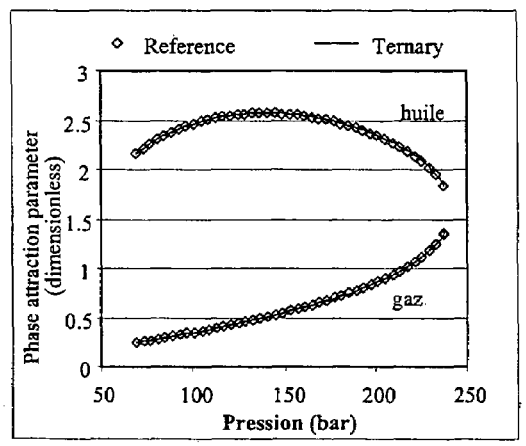
FIGS. 5 and 6 show, for the detailed and ternary representations, respectively the variation of the attraction term and of the covolume (expressed in dimensionless form) of the oil and gas phases as a function of the pressure during the thermodynamic simulation of a depressurization operation at constant volume at reservoir temperature, FIGS. 7A to 7P on the one hand and FIGS. 8A to 8P on the other hand show, per constituent, respectively the detailed composition of the gas and of the oil, during the same depressurization operation, as obtained from the reference representation, and from delumping of the three pseudo-component representation, FIG. 9 recapitulates the results illustrated in FIGS. 7A to 7P and 8A to 8P by showing the maximum absolute error obtained for the proportion of each constituent during the depressurization from 237.4 to 69 bars as a function of the proportion of constituent in the phase at the dew-point pressure of the initial fluid, FIGS. 10A to 10P on the one hand and FIGS. 11A to 11P on the other hand show, per constituent, respectively the detailed composition of the gas and of the oil, during the thermodynamic simulation of a condensate vaporization operation by injection of a dry gas at a constant pressure of 169 bars, as obtained from the reference representation, and from delumping of the three pseudo-component representation, and FIG. 12 recapitulates the results illustrated in FIGS. 10A to 10P and 11A to 11P by showing the maximum absolute error obtained for the proportion of each constituent for the vaporization operation as a function of the proportion of constituent in the phase at the beginning of the vaporization operation.

It can be observed that the BRO model provides a pressure solution that practically merges with the reference solution (with 16 constituents) and an oil saturation evolution solution in good agreement with the reference solution over the total simulated time. The grid used in FIG. 5 is the same one as the grid used in the reference paper by D. E. Kenyon and G. Alda Behie and in the paper by W. H. Goldthorpe mentioned in the prior art. It can be observed that the results of FIG. 4, judged by comparison with the results obtained by W. H. Goldthorpe with a BO modelling, show a much better quality of reproduction of the oil saturation evolution in the reservoir, whereas the procedure used to obtain the parameters of ECS_EQ is improvable.

ii) The results shown in FIGS. 2 and 3 for the oil flow rate and cumulative oil production throughout the simulated time show that the BRO modelling provides a solution that is very close to the reference solution.

The calculating time reduction provided by the BRO modelling is considerable, the acceleration factor being 46.

Delumping jj) We first represent the reservoir in form of a network of grid cells (m), each one forming an elementary volume filled with fluid(s) in form of one or more phases, with at least one non-aqueous phase. The non-aqueous phases are still referred to as hydrocarbon phases even though they may contain certain components other than hydrocarbons, such as nitrogen, carbon dioxide, sulfur dioxide.

kk) We define, for each thermodynamic zone or range, the fluid by a detailed representation with $N_{rb}$ components and/or pseudo-components. It can be noted that it is possible to treat the cases which require several thermodynamic representations, for example if several local thermodynamic paths can be distinguished during modelling (zones produced only by depressurization and zones subjected to gas injection can be distinguished). Several variation zones or ranges for the thermodynamic or compositional quantities, often referred to by specialists as thermodynamic zones, can thus be defined and used.

temperature ($T_m^t$) (if it varies), the molar flow rates per injection or production phase ($S_{gm}^t$) and ($S_{om}^t$), for each pair of grid cells (m,h), the molar flow rates of the liquid ($u_{omh}t$) and vapour ($u_{gmh}^t$) phases, the vapour fraction ($\theta_m^t$). These quantities are stored, as well as the parameters in state equation EOS_PRO for the liquid and vapour hydrocarbon phases (typically the covolumes and the attraction terms) involved in the expression of the equilibrium coefficients. In order to avoid recalculating them, the compressibility factors of the phases ($Z_{Om}^t$) and ($Z_{Gm}^t$) obtained by solution of state equation EOS_PRO can also be stored.

For a Peng-Robinson state equation, while keeping the notations introduced by equations (16), (17), (26) and (27), the phase parameters are denoted by ($b_{Om}^t$) and ($b_{Gm}^t$) for the covolumes of the phases, ($a_{Om}^t$) and ($a_{Gm}^t$),—or ($a_{1Om}^t$), ($a_{1Gm}^t$), ($a_{2Om}^t$), ($a_{2Gm}^t$) for the attraction terms of the phases.

The various parameters useful for equilibrium coefficients calculation, when mentioned in a general way, are denoted hereafter by ($E_{\pi P m}^t$), subscript P being for each oil and gas phase, and subscript $\pi$ a reference number for a particular parameter.

nn) We estimate at the time interval t+1 the molar fraction of each constituent i in the global detailed composition $$(z_{im}^{t+1})$$

of the hydrocarbon fluid in grid cell (m), knowing the number of moles of each constituent i in the detailed representation in each phase at the time interval t, respectively ($No_{im}^t$) for the oil phase and ($Ng_{im}^t$) for the gas phase from the equations hereafter:

$$No_m^t = \sum_i^{Nrb} No_{im}^t; \quad Ng_m^t = \sum_i^{Nrb} Ng_{im}^t; \quad N_m^t = No_m^t + Ng_m^t \quad (45)$$

$$x_{im}^t = \frac{No_{im}^t}{No_m^t}; \quad y_{im}^t = \frac{Ng_{im}^t}{Ng_m^t}; \quad z_{im}^t = \frac{No_{im}^t + Ng_{im}^t}{N_m^t} \quad (46)$$

$$z_{im}^{t+1} = \frac{z_{im}^t N_m^t - \Delta t(y_{im}^t, S_{gm}^t + x_{im}^t, S_{om}^t) - \Delta t \sum_{h \in J(m)} (y_{im}^t, u_{gmh}^t + x_{im}^t, u_{omh}^t)}{N_m^{t+1}} \quad (47)$$

$$N_m^{t+1} = N_m^t - \Delta t(S_{gm}^t + S_{om}^t) - \Delta t \sum_{h \in J(m)} (u_{gmh}^t + u_{omh}^t) \quad (48)$$

ll) Per thermodynamic zone for which we select a lumped representation of the fluids, we determine a state equation EOS_PRO constructed, prior to dynamic reservoir simulation with the lumped representation, to reproduce the phase parameters, in the state equation of the detailed representation, of the hydrocarbon fluids along thermodynamic paths considered to be representative of the paths that will be followed by the hydrocarbon fluids during the gridded simulation.

mm) We carry out, in a manner known in the art, a compositional simulation with a limited number of constituents where the phase properties are calculated by a state equation EOS_PRO, said simulation allowing to calculate at least in each grid cell (m), and at consecutive time intervals (t, t+1, etc.), a pressure in a hydrocarbon phase ($p_m^t$), the Equations (45) and (46) respectively allow to calculate, at time interval (t) and in grid cell (m), the number of moles per hydrocarbon phase and the global number $N_m^t$ from knowledge of the number of moles per constituent and per phase, the molar fractions of the constituents per phase and the global molar fractions.

Equation (48) translates the total hydrocarbon molar balance on grid cell (m), by taking account of the material exchanges, during time interval $\Delta t$, with all the grid cells (h) adjoining (m) which form set J(m).

In equation (47), the writing of terms ($y_{ij'}^{m}$,) and ($x_{ij'}^{m}$)—wherein m'=m for a flow rate from grid cell (m) to grid cell (h) or in the well, and m'=h for a flow rate from grid cell (h) to grid cell (m), and m' corresponding to the fluid injected in the case of injection wells, S being then negativeimplicitly implies the use of a simple upstream scheme for the compositional flows. A more general writing of these terms is $(y_{imh}^t)$ and $(x_{imh}^t)$, where $x_{imh}^t$ and $y_{imh}^t$ describe the compositions of the liquid and gas phases, obtained in a manner known in the art, flowing between grid cells (m) and (h).

oo) We determine, at time interval (t+1) and in each grid cell (m), the equilibrium coefficients $$(K_{im}^{t+1})$$

of constituent i in the detailed representation using a formulation explicitly involving parameters $E_{\pi P}$, by introducing therein the variable parameters $$(E_{\pi Pm}^{t+1})$$

resulting from the simulation with the lumped representation and, if need be, using some of the compositional variables described in the previous paragraph, calculated at time interval (t). Thus, for a Peng-Robinson state equation, the equilibrium coefficients given by equation (42) can be rewritten in the following form:

$$Ln(K_{im}^{t+1}) = D_{0m}^{t+1} + D_{1m}^{t+1} b_i + D_{2m}^{t+1} \sqrt{a_i(T_m^{t+1})} + \frac{P_m^{t+1}}{\sqrt{2} R^2 T_m^{t+1\,2}} I_{im}^{t+1} \quad (49)$$

with:

$$\begin{cases} D_{0m}^{t+1} = Ln\left(\frac{Z_{Gm}^{t+1} - B_{Gm}^{t+1}}{Z_{Om}^{t+1} - B_{Om}^{t+1}}\right) \\ L_{Pm}^{t+1} = Ln\left(\frac{Z_{Pm}^{t+1} + (1+\sqrt{2})B_{Pm}^{t+1}}{Z_{Pm}^{t+1} + (1-\sqrt{2})B_{Pm}^{t+1}}\right) \quad P = O, G \\ D_{1m}^{t+1} = \frac{P_m^{t+1}}{RT_m^{t+1}}\left[\frac{Z_{Om}^{t+1} - 1}{B_{Om}^{t+1}} - \frac{Z_{Gm}^{t+1} - 1}{B_{Gm}^{t+1}} + \frac{A_{Om}^{t+1} L_{Om}^{t+1}}{2\sqrt{2} B_{Om}^{t+1\,2}} - \frac{A_{Gm}^{t+1} L_{Gm}^{t+1}}{2\sqrt{2} B_{Gm}^{t+1\,2}}\right] \\ D_{2m}^{t+1} = \frac{P_m^{t+1}}{\sqrt{2} R^2 T_m^{t+1\,2}}\left[\frac{L_{Gm}^{t+1}}{B_{Gm}^{t+1}} a_{1Gm}^{t+1} - \frac{L_{Om}^{t+1}}{B_{Om}^{t+1}} a_{1Om}^{t+1}\right] \end{cases} \quad (50)$$

Equations (50) involve the dimensionless phase parameters B and A previously defined by equations (19) and (20).

In equation (49), term $$I_{im}^{t+1}$$

represents the contribution of the binary interactions between constituents and this term is zero when the binary interaction coefficients of the detailed representation are all zero. In such a case, the equilibrium coefficients can be calculated directly from parameters $$(E_{\pi Pm}^{t+1})$$

from the state equation EOS_PRO of the dynamic simulation using the lumped representation.

In the opposite case, a rigorous expression for term $$I_{im}^{t+1}$$

is:

$$I_{im}^{t+1} = \frac{L_{Om}^{t+1}}{B_{Om}^{t+1}} \sum_{j=1}^{Nrb}\left[\sqrt{a_i(T_m^{t+1})}\sqrt{a_j(T_m^{t+1})}\delta_{ij} x_{jm}^{t+1}\right] - \frac{L_{Gm}^{t+1}}{B_{Gm}^{t+1}} \sum_{j=1}^{Nrb}\left[\sqrt{a_i(T_m^{t+1})}\sqrt{a_j(T_m^{t+1})}\delta_{ij} y_{jm}^{t+1}\right] \quad (51)$$

This term thus involves the molar fractions, in the detailed representation, of the constituents in the hydrocarbon phases at time interval (t+1)

$$x_{im}^{t+1}, y_{im}^{t+1},$$

not estimated yet. In order to avoid a heavy implicit resolution, it is possible, in equation (51), to substitute the molar fractions $$x_{im}^{t+1}, y_{im}^{t+1}$$

for the molar fractions at time interval (t) from equations (46).

Figure 9:
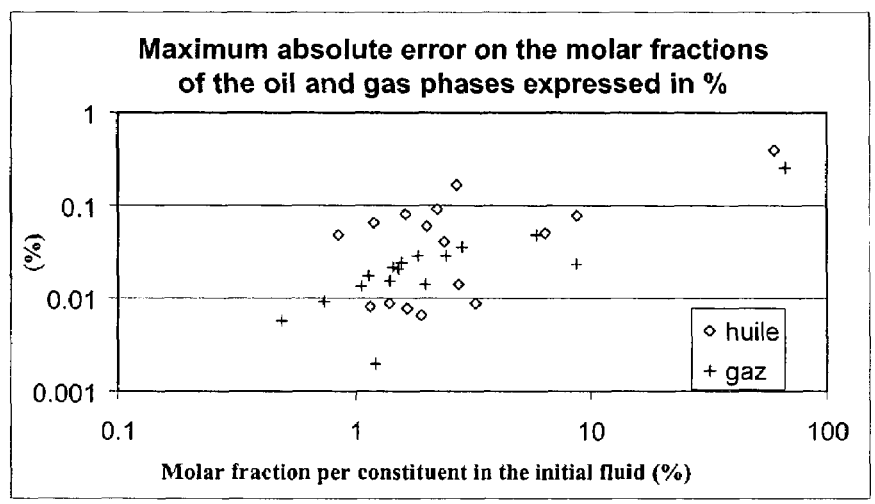
Figure 10A:
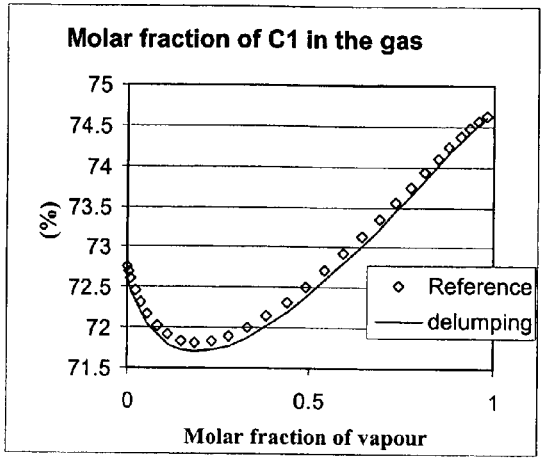
Figure 11A:
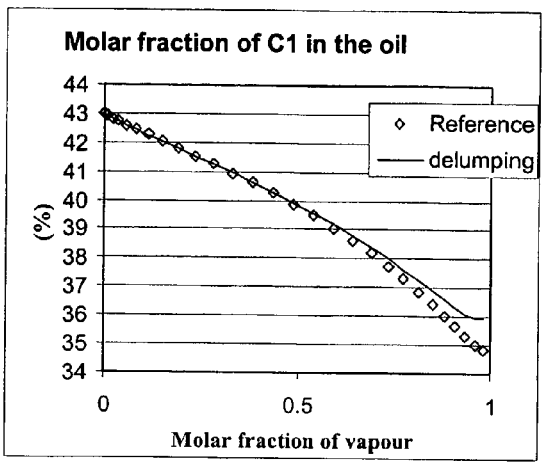
Figure 10B:
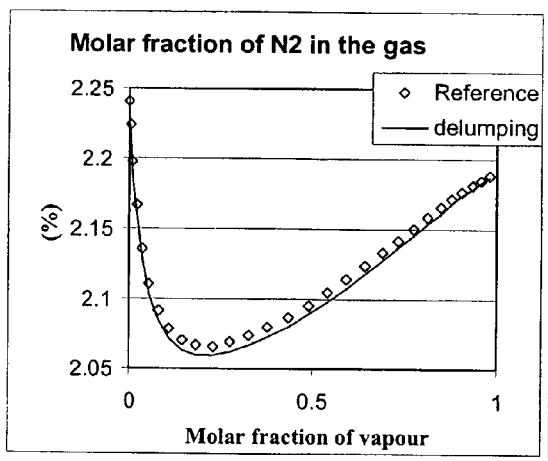
Figure 11B:
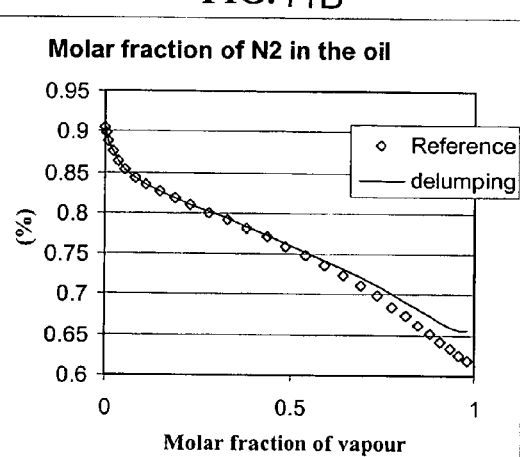
Figure 10C:
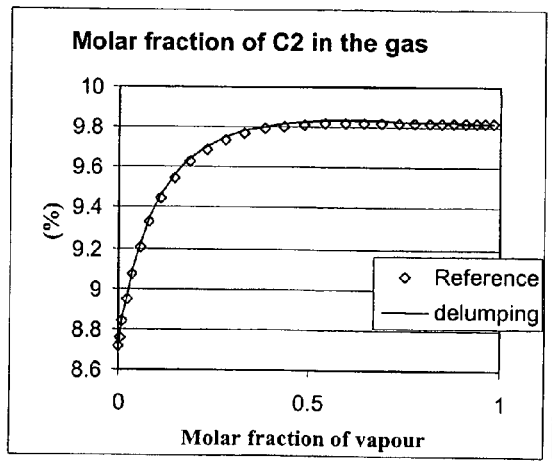
Figure 11C:
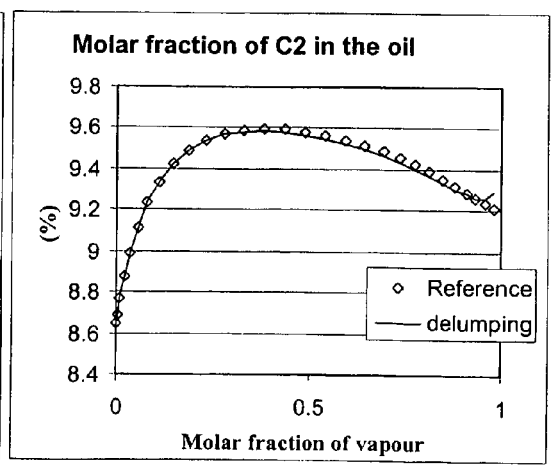
Figure 10D:
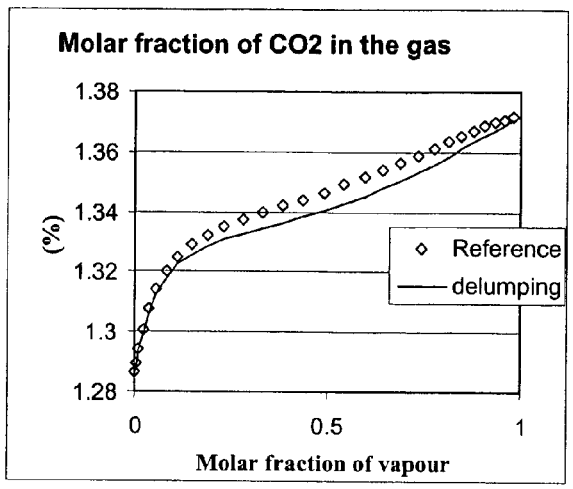
Figure 11D:
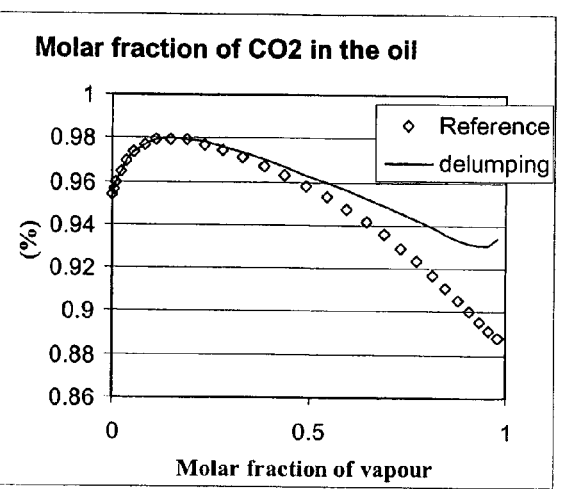
Figure 10E:
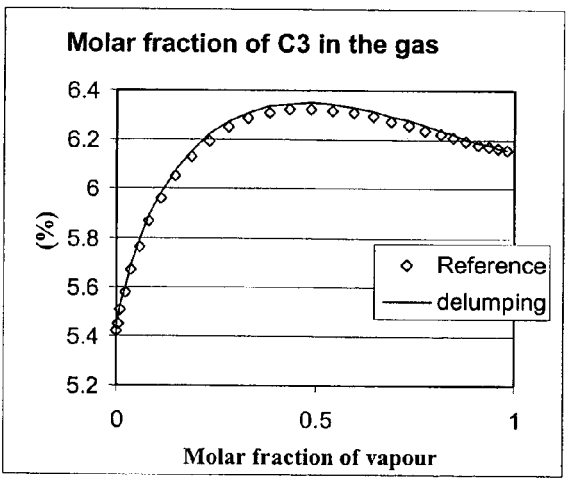
Figure 11E:
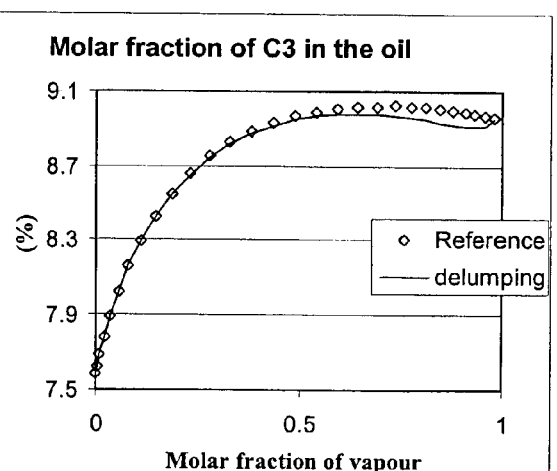
Figure 10F:
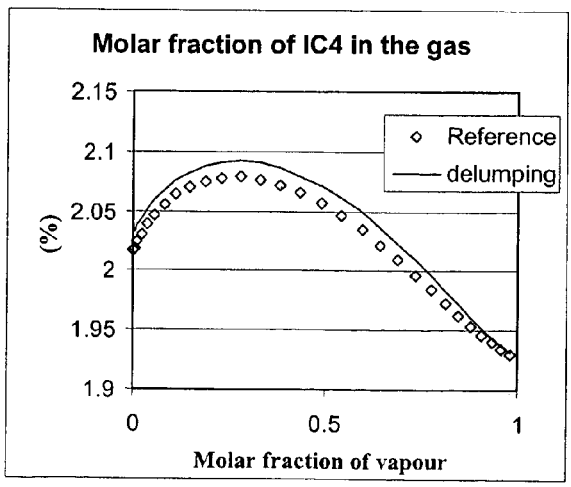
Figure 11F:
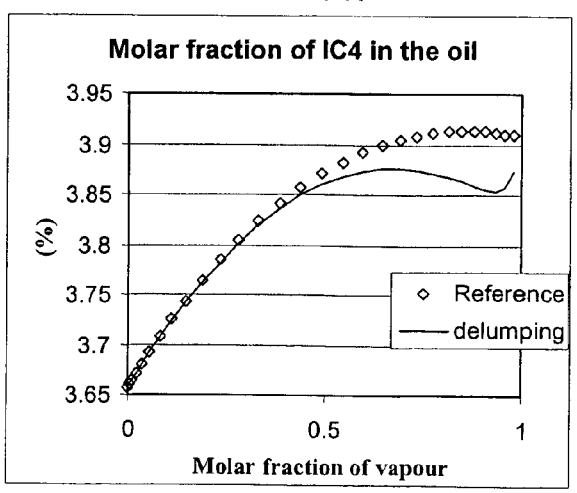
Figure 10G:
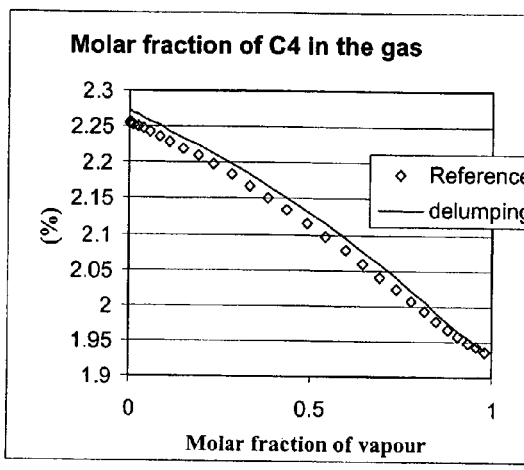
Figure 11G:
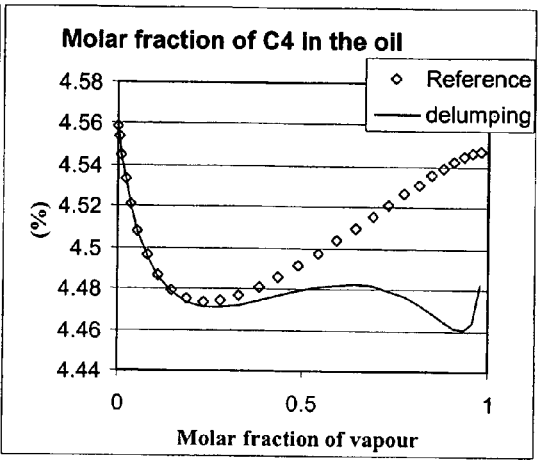
Figure 10H:
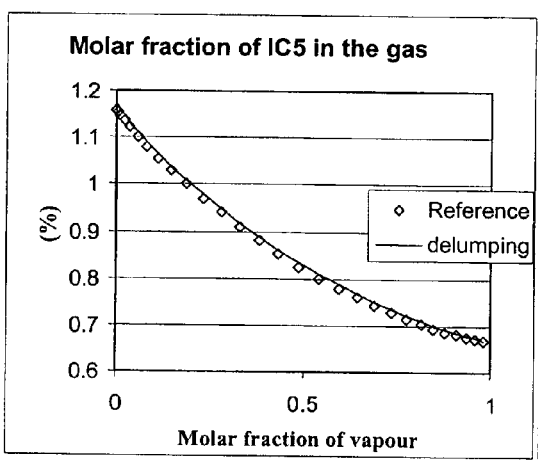
Figure 11H:
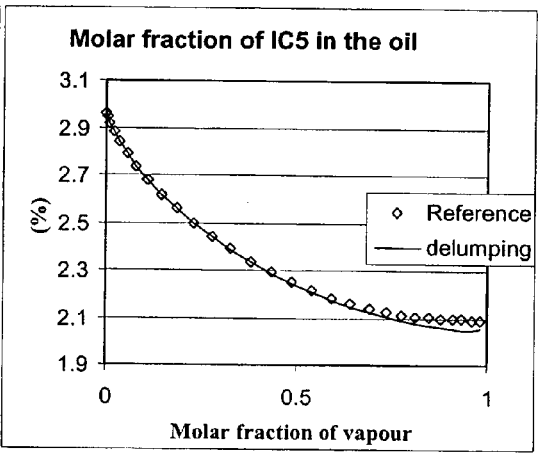
Figure 10I:
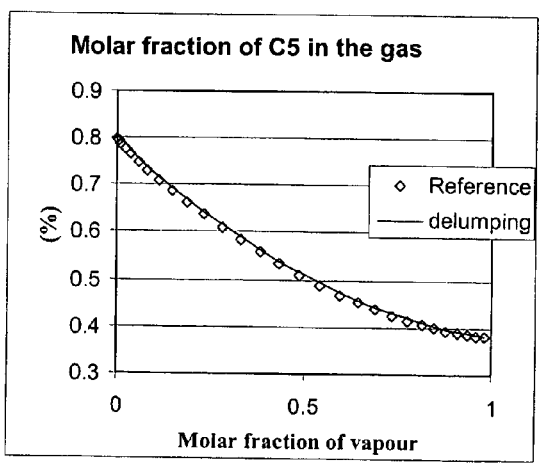
Figure 11I:
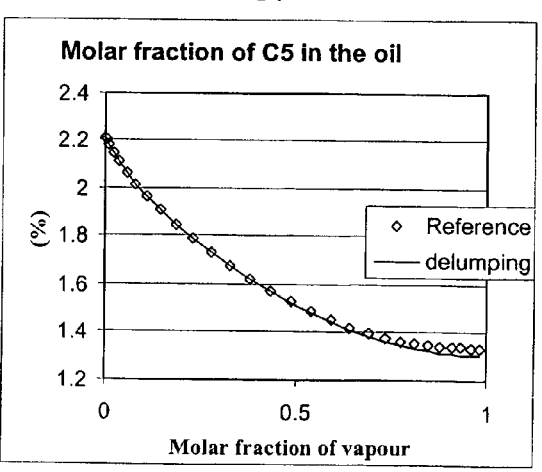
Figure 10J:
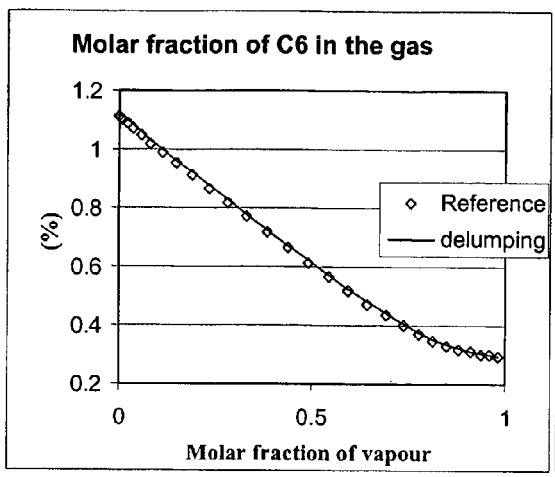
Figure 11J:
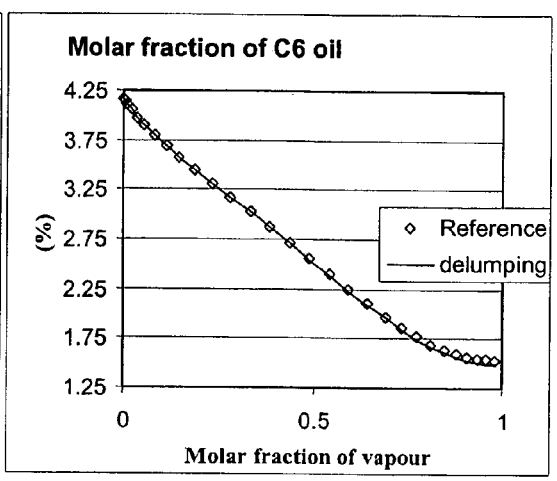
Figure 10K:
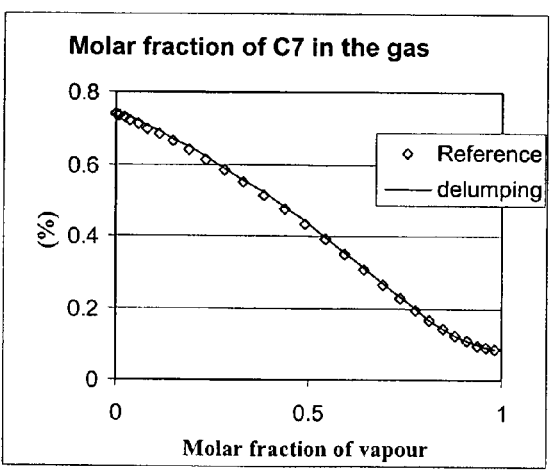
Figure 11K:
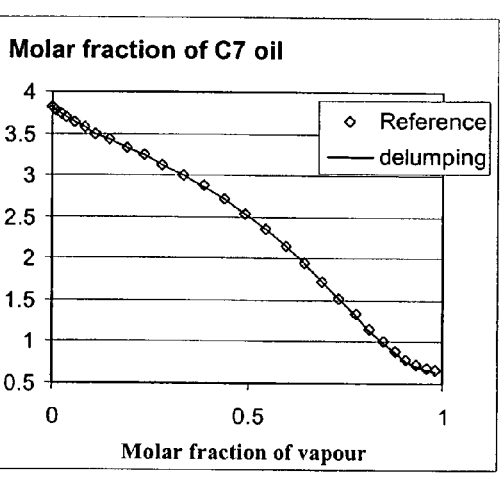
Figure 10L:
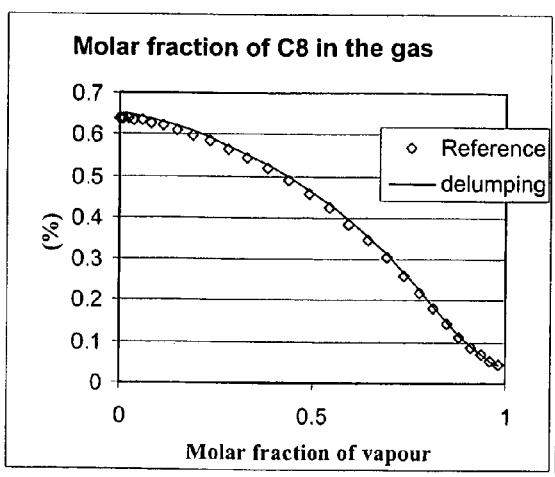
Figure 11L:
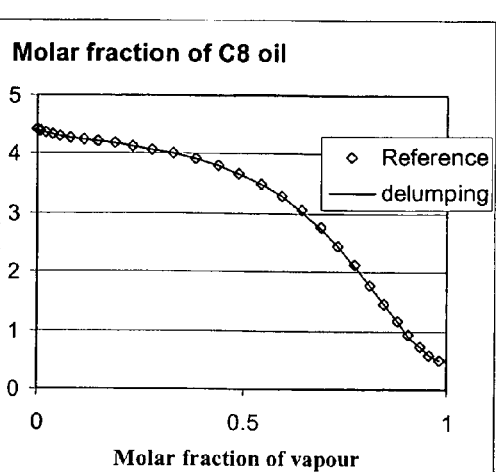
Figure 10M:
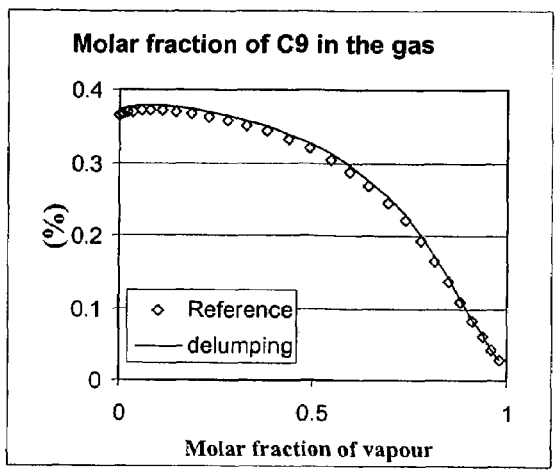
Figure 11M:
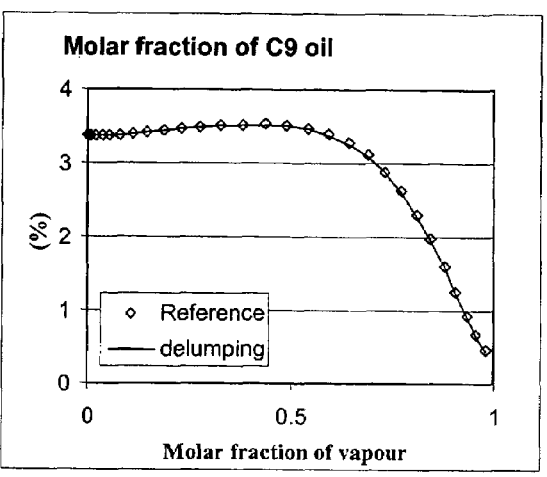
Figure 10N:
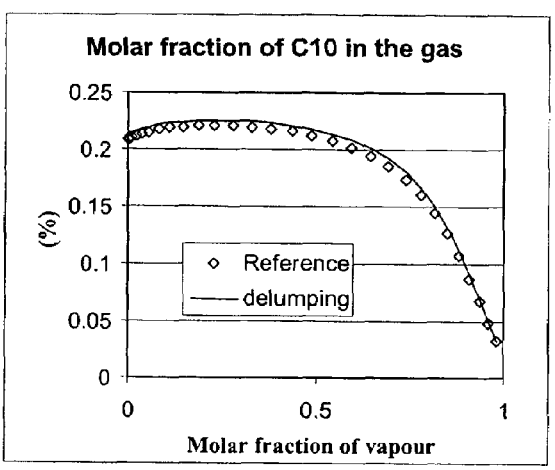
Figure 11N:
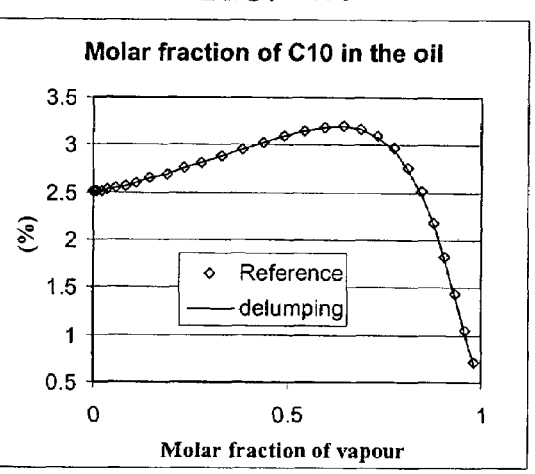
Figure 10O:
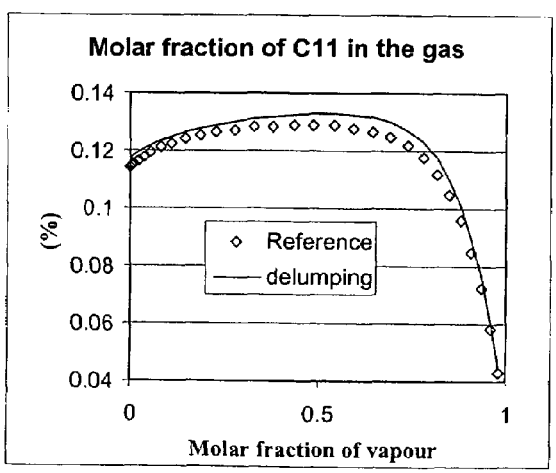
Figure 11O:
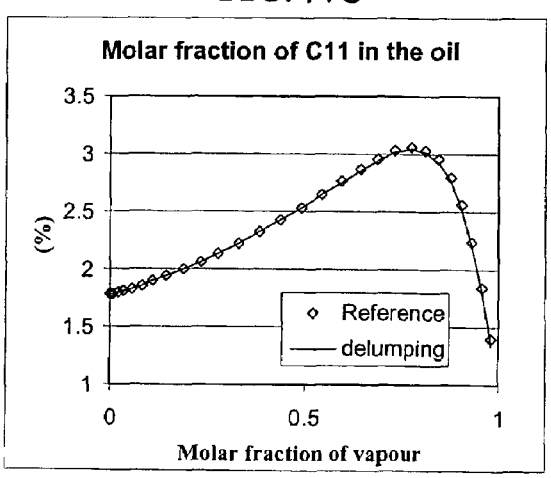
Figure 10P:
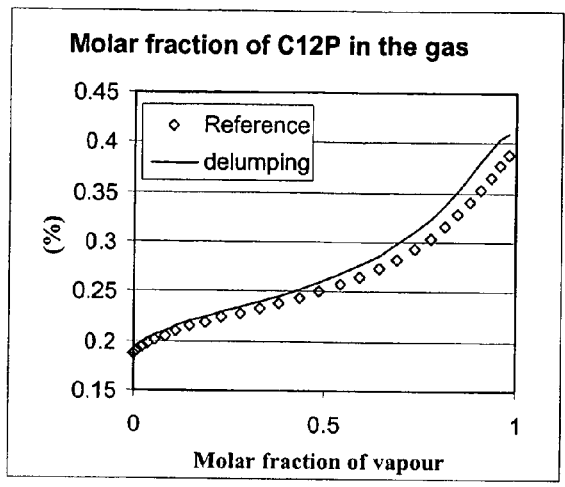
Figure 11P:
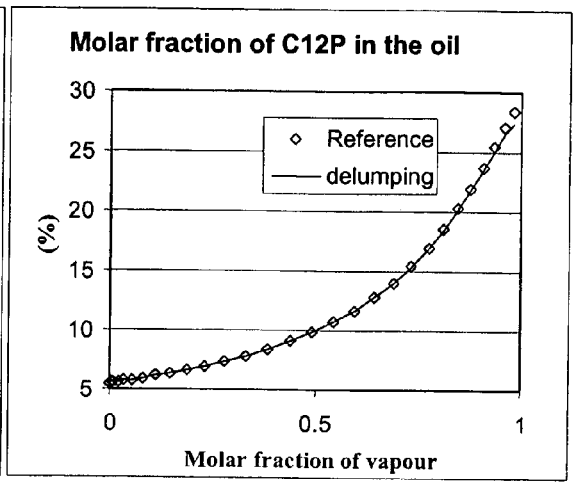
Figure 12:
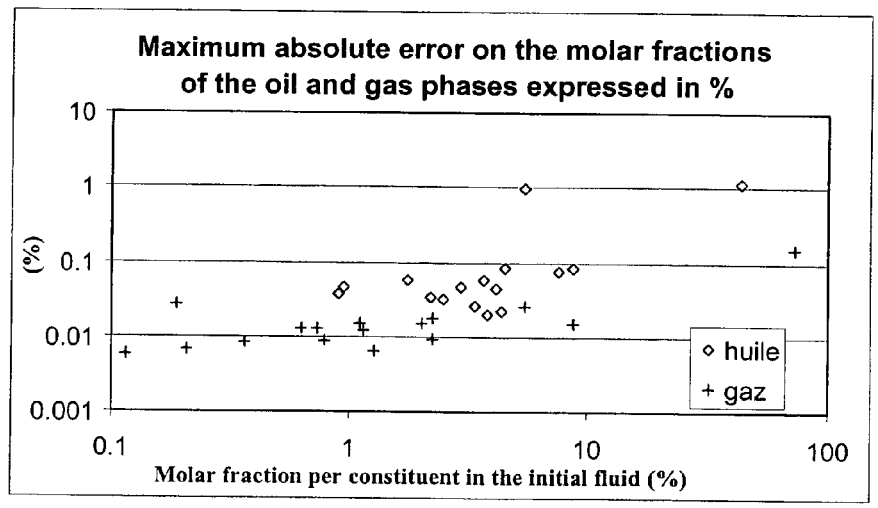

It is with such a non limitative approximation that the delumping results:

illustrated in FIGS. 7A to 7P, FIGS. 8A to 8P and recapitulated in FIG. 9 for a depressurization operation of the fluid of the SPE3 case, illustrated in FIGS. 10A to 10P, FIGS. 11A to 11P and recapitulated in FIG. 12 for a vaporization operation at a pressure of 169 bars of a condensate (the condensate obtained at 169 bars during the previous depressurization operation), were obtained.

In FIGS. 7A to 7P and 8A to 8P on the one hand, FIGS. 10A to 10P and 11A to 11P on the other hand, the proportion of each constituent in the phase considered is expressed in molar percentage of the phase and, in each figure, the scale is expanded to be suited to the variation of the proportion of constituent in the phase.

The abscissa in FIGS. 10A to 10P and FIGS. 11A to 11P is the molar fraction of vapour during the vaporization operation, which increases from 0 (in the initial state, only the condensate phase, or oil, is present) to 1 when all of the condensate is vaporized.

FIG. 9 and FIG. 12 show that the maximum absolute error obtained for the proportion of each constituent (still expressed in molar percentage) remains below 0.1% on average during the depressurization and vaporization operations.

We thus observe that the compositions resulting from the delumping operation are consistent with the detailed reference compositions of the fluids, although the approximation used is not among the most sophisticated ones.

Another possible, still non limitative approximation consists in estimating the molar fractions $$x_{im}^{t+1}, y_{im}^{t+1}$$

from the equilibrium coefficients $K_{im}{}^t$ that can be calculated from the molar fractions given by equations (46) by $$\begin{cases} x_{im}^{t+1} = \frac{z_{im}^{t+1}(K_{im}^t - 1)}{1 + (K_{im}^t - 1)\theta_m^{t+1}} \\ y_{im}^{t+1} = \frac{k_{im}^t z_{im}^{t+1}(K_{im}^t - 1)}{1 + (K_{im}^t - 1)\theta_m^{t+1}} \end{cases} \quad (52)$$

In general, the binary interaction coefficients are small in relation to 1, and an iterative calculation, for example by successive substitutions, is not necessary but remains possible.

pp) We determine, at each time interval (t+1), the vaporized fraction $$(\theta_m^{t+1})$$

in each grid cell (m), either from the results of the dynamic simulation with the lumped representation or, if a higher precision is desired, by solving the Rachford-Rice equation, from the molar fractions of each component i in the global detailed composition $$(z_{im}^{t+1})$$

of the hydrocarbon fluid in grid cell (m) at time interval (t+1).

$$\sum_{i=1}^{Nrb} \frac{z_{im}^{t+1}(K_{im}^{t+1} - 1)}{1 + (K_{im}^{t+1} - 1)\theta_m^{t+1}} = 0 \quad (53)$$

The numbers of moles per phase in each grid cell at time interval (t+1) are given by:

$$No_m^{t+1} = N_m^{t+1}(1 - \theta_m^{t+1}); \quad Ng_{im}^{t+1}\theta_m^{t+1} \quad (54)$$

qq) We estimate the detailed composition of each hydrocarbon phase, at each time interval (t+1) and in each grid cell (m), using the following relations:

$$x_{im}^{t+1} = \frac{z_{im}^{t+1}(K_{im}^{t+1} - 1)}{1 + (K_{im}^{t+1} - 1)\theta_m^{t+1}} \text{ for the oil phase} \quad (55)$$

$$y_{im}^{t+1} = \frac{K_{im}^{t+1} z_{im}^{t+1}(K_{im}^{t+1} - 1)}{1 + (K_{im}^{t+1} - 1)\theta_m^{t+1}} \text{ for the gas phase} \quad (56)$$

rr) Finally, we obtain the numbers of moles of each constituent i in the detailed representation in each phase at time interval (t+1), respectively $$(No_{im}^{t+1})$$

for the oil phase and $$(Ng_{im}^{t+1})$$

by equations (46) modified into:

$$No_{im}^{t+1} = No_m^{t+1} x_{im}^{t+1}; \quad Ng_{im}^{t+1} = Ng_m^{t+1} y_{im}^{t+1} \quad (57)$$

ss) Paragraphs nn) to rr) detail the content of the operations for shifting from time interval t to time interval t+1, assuming that the numbers of moles of each constituent i in the detailed representation in each phase at time interval t in each grid cell of the simulation with the lumped representation, respectively denoted by $(No_{im}{}^t)$ for the oil phase and and $(Ng_{im}{}^t)$ for the gas phase, are known. To start calculation, these quantities just have to be known at a given time or time interval; which can be in particular the initial time. This can be obtained by various means known in the art, one means consisting in an initialization calculation of a compositional simulation (calculation of the initial state only) using the detailed compositional representation, the inputs other than compositional being the same as for the compositional simulation with the lumped representation.

We then know how to describe the evolution of the detailed composition in each grid cell during the production process modelled in a compositional model using a lumped representation by means of a memory of the parameters of the state equation of the detailed representation kept in the phase properties calculation method.

Some calculation stages may appear unnecessary because redundant. Some of these redundancies have the advantage of allowing to reduce the storage space required for data storage, but they can obviously be avoided if the storage space considerations are not a priority.

In the case where EOS_PRO is valid for calculation of the equilibrium coefficients (Ki, m and t+1), delumping of the results of a reservoir simulation carried out with the method according to the invention can be performed by applying the method described in the aforementioned patent WO/42,937.

Comments Concerning the Generalization of the Approach tt) The details provided in the description of the method use a molar formalism; a mass formalism could also be used.

uu) It can be noted that the line of reasoning based on the master hypothesis "M" described in paragraph d), applied to the set constituents of the base representation, a set referred to hereafter as "B", in the previous paragraphs, could have been alternatively applied to a subset of the constituents of the base representation, referred to as "R" hereafter. The complementary set of "R" in "B" being denoted by "S", equations (5) would then be rewritten (with P=O,G) as $$\begin{cases} MM_{PO}^e = x_{PI}^e MM_I + x_{PH}^e MM_H + \sum_{i}^{i \in S} x_{Pi}^e MM_i; & x_{PI}^e + x_{PH}^e = 1 - \sum_{i}^{i \in S} x_{Pi}^e \\ MM_{PG}^e = y_{PV}^e MM_V + y_{PI}^e MM_I + \sum_{i}^{i \in S} y_{Pi}^e MM_i; & y_{PV}^e + y_{PI}^e = 1 - \sum_{i}^{i \in S} y_{Pi}^e \end{cases} \quad (58)$$

Such an approach can be interesting when, for the case treated, it is necessary to keep explicit certain base constituents in the lumped representation. Thus, in a practical case where the reservoir conditions would not allow to disregard the dissolution of some constituents (such as carbon dioxide) in water, these constituents could form set "S".

The simple variable changes given hereafter allow to bring equations (5) back to the situation where the set of constituents of the base representation has been considered:

$$\begin{cases} MM_{PO}^e \big|_R = \dfrac{MM_{PO}^e - \sum_{i}^{i \in S} x_{Pi}^e MM_i}{1 - \sum_{i}^{i \in S} x_{Pi}^e}; & MM_{PG}^e \big|_R = \dfrac{MM_{PG}^e - \sum_{i}^{i \in S} y_{Pi}^e MM_i}{1 - \sum_{i}^{i \in S} y_{Pi}^e} \\ x_{PI}^e \big|_R = \dfrac{x_{PI}^e}{1 - \sum_{i}^{i \in S} x_{Pi}^e}; & x_{PH}^e \big|_R = \dfrac{x_{PH}^e}{1 - \sum_{i}^{i \in S} x_{Pi}^e}; & y_{PV}^e \big|_R = \dfrac{y_{PV}^e}{1 - \sum_{i}^{i \in S} y_{Pi}^e}; & y_{PI}^e \big|_R = \dfrac{y_{PI}^e}{1 - \sum_{i}^{i \in S} y_{Pi}^e}; \end{cases} \quad (59)$$

Equations (6) being solved with the new variables, an inverse transformation of variables then allows to carry out one after the other the calculations of paragraph g) and the following paragraphs.

The lumped representation then comprises constituents (V), (I), (H) and the base constituents of set "S". In each phase of set "E", the molar fractions of the base constituents forming set "S" are the same in the lumped representation as in the base representation.

vv) The compositions of the phases of set "E" in the lumped representation being thus obtained, the broad lines of the stages described above can be followed to model the phase properties and the thermodynamic equilibria. From the moment that a state equation is sought for modelling with the lumped representation the phase properties and/or the thermodynamic equilibria, the indication is to retain for the base constituents forming set "S" the parameters of these constituents in the state equation of the detailed description. The only parameters to be estimated are then the parameters of constituents (V), (I), (H) in the state equation, and if need be the parameters of the binary interactions of these constituents with the constituents of set "S". When the latter are considered to be zero, the guiding line followed throughout paragraphs n) to w) can be followed, which consists in seeking the state equation parameters EOS_PRO useful for calculation, under the reservoir conditions, of the phase densities (via the compressibility factors) and of the viscosities by simple solutions (non iterative) of systems of linear equations.

The invention claimed is:

1. A method for projecting dimensioning and management of surface installations of a hydrocarbon reservoir under production, by means of a lumping method for estimating the properties or the behavior of fluids comprising liquid and/or vapor hydrocarbon phases from data relative to a reference set consisting of hydrocarbon mixtures in a series of thermodynamic states resulting from determined conditions of production of the hydrocarbon reservoir, characterized in that it comprises:

grouping each one of said hydrocarbon mixtures into at least three constituents (V, I, H), none of these constituents corresponding to a particular selection of base components or pseudo-components that would be used for a detailed compositional description of the fluids, considering that the gas phases resulting from separation under surface conditions of each one of the hydrocarbon mixtures are mixtures from which third constituent (H) is excluded, and that the oil phases resulting from the separation under surface conditions of each one of the hydrocarbon mixtures are mixtures from which first constituent (V) is excluded, determining by material balance the compositions of the separation products comprising, for the gaseous products, at least the first and the second constituent (V, I) in variable proportions and, for the liquid products, at least the second and the third constituent (I, H) in variable proportions, determining the at least three-constituent composition of each hydrocarbon mixture of the reference set by combination of the products of the separation thereof in proportion to the amounts of each separation product, simulating a production of the hydrocarbon reservoir while establishing detailed compositional profiles from the at least three-constituent composition, and projecting dimensioning and management of the surface installations from the simulated production of the hydrocarbon reservoir.

2. A method as claimed in claim 1, wherein each one of the hydrocarbon mixtures is grouped into only three constituents (V, I, H), the gas phases resulting from said separation being mixtures in variable proportions of first constituent (V) and of second constituent (I), the oil phases resulting from said separation are mixtures in variable proportions of second constituent (I) and of third constituent (H), and the three-constituent composition is determined.

3. A method as claimed in claim 1, wherein the surface conditions are the conditions encountered or expected during reservoir production.

4. A method as claimed in claim 1, wherein the surface conditions are different from the conditions encountered or expected during reservoir production.

5. A method as claimed in claim 1, wherein the material balance is a mass balance and a molar mass is assigned to each one of the three constituents (V, I, H) after quantitative analysis of the molar masses of the separation products of the reference set.

6. A method as claimed in claim 1, wherein the data necessary for equilibrium calculation and for modeling the phase properties in the lumped representation are defined using the compositions of the phases in the lumped representation and known or estimated a priori data relative to at least the density and the viscosity of the oil and gas phases at equilibrium belonging to the reference set.

7. A method as claimed in claim 6 wherein, when said data includes detailed compositional data of the phases previously represented by a state equation, the parameters of a first state equation of the lumped representation, used for modeling the phase properties, are defined using this compositional data.

8. A method as claimed in claim 7, wherein the parameters of a second state equation of the lumped representation, useful for equilibrium calculations, are adjusted in order to reproduce the equilibrium coefficients of the lumped representation.

9. A method as claimed in claim 8, wherein the parameters per constituent of the lumped representation in the first state equation are used in the adjustment procedure for defining the parameters of the second state equation of the lumped representation useful for equilibrium calculations.

10. A method as claimed in claim 1, wherein the equilibrium coefficients of the fluids are determined in a detailed compositional representation, from variables and/or parameters involved in the calculation of the phase properties, from the moment that the parameters useful for calculation of the phase properties in the lumped representation have been estimated so as to reproduce the parameters of the phases in the state equation of the detailed compositional description.

11. A method as claimed in claim 1, comprising delumping for predicting as a function of time, and in at least one thermodynamic zone, a detailed composition of a fluid contained in a hydrocarbon reservoir or produced by at least one well.

12. A method as claimed in claim 11, comprising:

representing the reservoir in the form of a network of grid cells (m) wherein each one forms an elementary volume filled with fluids in form of one or more phases, with at least one non-aqueous phase, defining, for each thermodynamic zone or range, the fluids by a detailed base representation, so as to determine the amount of each base constituent (i) in each hydrocarbon phase in each grid cell (m) at the time defined as initial for the delumping calculation, per thermodynamic zone for which a lumped representation of the fluids is selected, determining a state equation constructed prior to dynamic reservoir simulation with the lumped representation, to reproduce the phase parameters, in the state equation of the detailed representation, of the hydrocarbon fluids along thermodynamic paths considered to be representative of those that will be followed by the hydrocarbon fluids during the gridded simulation, carrying out, at a time interval t, a compositional simulation with a limited number of constituents wherein the phase properties are calculated by a state equation, said simulation allowing to calculate at least in each grid cell (m) and at consecutive time intervals a pressure for a hydrocarbon phase, the temperature when it varies, the flow rates of the phases between grid cells and at the production and injection perforations, and the values of parameters and/or phase properties involved in the formal expression of the equilibrium coefficients of the detailed representation, and storing these various quantities, estimating at the next time interval (t+1) the molar fraction of each constituent i in the global detailed composition of the hydrocarbon fluid in grid cell (m) by material balance on grid cell (m), determining, using the quantities stored, at the same time interval (t+1) and in each grid cell (in), the equilibrium coefficients of each constituent (i) in the detailed representation, determining, in the same time interval (t+1), the vaporized fraction in each grid cell (m), and estimating the detailed composition of each hydrocarbon phase, at the same time interval (t+1) and in each grid cell (m).

13. A method as claimed in claim 1, wherein various stages are translated so as to produce intermediate or final results usable in equations expressed according to a molar or mass formalism.

* * * * *